United States Patent
Reznikoff et al.

(10) Patent No.: US 6,437,109 B1
(45) Date of Patent: *Aug. 20, 2002

(54) SYSTEM FOR *IN VITRO* TRANSPOSITION

(75) Inventors: William S. Reznikoff, Maple Bluff; Igor Yu Goryshin; Hong Zhou, both of Madison, all of WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/272,432

(22) Filed: Mar. 19, 1999

Related U.S. Application Data

(60) Division of application No. 08/850,880, filed on May 2, 1997, now Pat. No. 5,925,545, which is a continuation-in-part of application No. 08/814,877, filed on Sep. 9, 1996, now Pat. No. 5,965,443.

(51) Int. Cl.$^7$ ............................................... C07H 21/04
(52) U.S. Cl. ..................................................... 536/23.1
(58) Field of Search ....................................... 536/23.1

(56) References Cited

U.S. PATENT DOCUMENTS

| | | | | |
|---|---|---|---|---|
| 5,316,946 A | * | 5/1994 | Phadnis et al. | 435/320.1 |
| 5,948,622 A | * | 9/1999 | Reznikoff et al. | 435/6 |

OTHER PUBLICATIONS

Benjamin, Howard W., "Excision of Tn10 from the donor site during transposition occurs by flush double–strand cleavages at the transposon termini," *Proc. Natl. Acad. Sci. USA*, 89:4648–4652 (May 1992).

Craigie, Robert, et al., "A defined system for the DNA strand–transfer reaction at the initiation of bacteriophage Mu transposition: Protein and DNA substrate requirements," *Proc. Natl. Acad. Sci. USA*, 82:7570–7574 (Nov. 1985).

de la Cruz, Norberto B., et al., "Characterization of the TN5 Transposase and Inhibitor Proteins: a Model for the Inhibition of Transposition," *Journal of Bacterioilogy*, 175(21):6932–6938. (Nov. 1993).

Delong et al., "Trans–acting Transposase Mutant from Tn5" *Proc. Natl. Acad. Sci. USA* 88(14):6072–6076 (1991).

Jilk, Ross Alan, et al., "The Organization of the Outside End of Transposon Tn5," *Journal of Bacteriology*, 178(6):1671–1679 (Mar. 1996).

Johnson et al., "DNA Sequences at the Ends of Transposon Tn5 Required for Transposition", *Nature* 304(21):280–282 (1983).

Lavoie, B.D., et al., "Transposition of Phage Mu DNA," Dept. Of Biochemistry, Jniv. of Western Ontario.

Mizuuchi, Kiyoshi, "In Vitro Transposition of Bacteriophage Mu: A Biochemical Approach to a Novel Replication Reaction," *Cell*, 35:785–794 (Dec. 1983).

Morisata, Donald, et al., "TN10 Transposition and Circle Formation In Vitro," *Cell*, 51:101–111 (Oct. 9, 1987).

Sakai, Janice, et al., "Identification and characterization of a pre–cleavage synaptic complex that is an early intermediate in TN10 transposition,"*The EMBO Journal*, 14(17):4374–4383 (1995).

Weinreich, Michael D., "A Functional Analysis of the TN5 Transposase: Identification of Domains Required for DNA Binding and Multimerization," *J. Mol. Biol.*, 241:166–177 (1994).

Weinreich, Michael D., et al., "Evidence that the cis preference of the Tn5 transposase is caused by nonproductive multimerization," *Genes & Development*, 8:2363–2374 (1994).

Wiegand, Torsten W., et al., "Characterization of Two Hypertransposing Tn5 Mutants," *Journal of Bacteriology*, 174(4):1229–1239 (Feb. 1992).

Wiegand et al., "Transposase Mutants That Increase the Transposition Frequency of Tn5", PhD Thesis (Abstract) University of Wisconsin–Madison (1993).

Zhou et al., "Three Types of Novel Mutations in the NH–2–Terminus of Tn5 Transposase: Structure–function of Transposase", Keystone Symposium on Transposition and Site–Specific Recombination: Mechanism and Biology (Abstract) Jan. 1994. J. of Cell. Biochem. Suppl. O(18B) (1994).

\* cited by examiner

*Primary Examiner*—Terry McKelvey
*Assistant Examiner*—William Sandals
(74) *Attorney, Agent, or Firm*—Quarles & Brady LLP

(57) ABSTRACT

A system for in vitro transposition includes a donor DNA that includes a transposable element flanked by a pair of bacterial transposon Tn5 outside end repeat sequences, a target DNA into which the transposable element can transpose, and a modified Tn5 transposase having higher binding avidity to the outside end repeat sequences and being less likely to assume an inactive multimer form than wild type Tn5 transposase.

7 Claims, 8 Drawing Sheets

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1534 base pairs
      (B) TYPE: nucleic acid
      (C) STRANDEDNESS: double
      (D) TOPOLOGY: linear (ii) MOLECULE TYPE: other nucleic acid
      (A) DESCRIPTION: /desc = "Gene encoding modified Tn5
          transposase enzyme"

(ix) FEATURE:
      (A) NAME/KEY: CDS
      (B) LOCATION: 93..1523

(xi) SEQUENCE DESCRIPTION: SEQ ID NO:1:

```
CTGACTCTTA TACACAAGTA GCGTCCTGAA CGGAACCTTT CCCGTTTTCC AGGATCTGAT          60

CTTCCATGTG ACCTCCTAAC ATGGTAACGT TC ATG ATA ACT TCT GCT CTT CAT          113
                                   Met Ile Thr Ser Ala Leu His
                                    1               5

CGT GCG GCC GAC TGG GCT AAA TCT GTG TTC TCT TCG GCG GCG CTG GGT          161
Arg Ala Ala Asp Trp Ala Lys Ser Val Phe Ser Ser Ala Ala Leu Gly
         10                  15                  20

GAT CCT CGC CGT ACT GCC CGC TTG GTT AAC GTC GCC GCC CAA TTG GCA          209
Asp Pro Arg Arg Thr Ala Arg Leu Val Asn Val Ala Ala Gln Leu Ala
     25                  30                  35

AAA TAT TCT GGT AAA TCA ATA ACC ATC TCA TCA GAG GGT AGT AAA GCC          257
Lys Tyr Ser Gly Lys Ser Ile Thr Ile Ser Ser Glu Gly Ser Lys Ala
 40                  45                  50                  55

GCC CAG GAA GGC GCT TAC CGA TTT ATC CGC AAT CCC AAC GTT TCT GCC          305
Ala Gln Glu Gly Ala Tyr Arg Phe Ile Arg Asn Pro Asn Val Ser Ala
                 60                  65                  70

GAG GCG ATC AGA AAG GCT GGC GCC ATG CAA ACA GTC AAG TTG GCT CAG          353
Glu Ala Ile Arg Lys Ala Gly Ala Met Gln Thr Val Lys Leu Ala Gln
             75                  80                  85

GAG TTT CCC GAA CTG CTG GCC ATT GAG GAC ACC ACC TCT TTG AGT TAT          401
```

```
                                                                -continued

Glu Phe Pro Glu Leu Leu Ala Ile Glu Asp Thr Thr Ser Leu Ser Tyr
         90                  95                 100

CGC CAC CAG GTC GCC GAA GAG CTT GGC AAG CTG GGC TCT ATT CAG GAT      449
Arg His Gln Val Ala Glu Glu Leu Gly Lys Leu Gly Ser Ile Gln Asp
        105                 110                 115

AAA TCC CGC GGA TGG TGG GTT CAC TCC GTT CTC TTG CTC GAG GCC ACC      497
Lys Ser Arg Gly Trp Trp Val His Ser Val Leu Leu Leu Glu Ala Thr
120                 125                 130                 135

ACA TTC CGC ACC GTA GGA TTA CTG CAT CAG GAG TGG TGG ATG CGC CCG      545
Thr Phe Arg Thr Val Gly Leu Leu His Gln Glu Trp Trp Met Arg Pro
                140                 145                 150

GAT GAC CCT GCC GAT GCG GAT GAA AAG GAG AGT GGC AAA TGG CTG GCA      593
Asp Asp Pro Ala Asp Ala Asp Glu Lys Glu Ser Gly Lys Trp Leu Ala
            155                 160                 165

GCG GCC GCA ACT AGC CGG TTA CGC ATG GGC AGC ATG ATG AGC AAC GTG      641
Ala Ala Ala Thr Ser Arg Leu Arg Met Gly Ser Met Met Ser Asn Val
        170                 175                 180

ATT GCG GTC TGT GAC CGC GAA GCC GAT ATT CAT GCT TAT CTG CAG GAC      689
Ile Ala Val Cys Asp Arg Glu Ala Asp Ile His Ala Tyr Leu Gln Asp
    185                 190                 195

AGG CTG GCG CAT AAC GAG CGC TTC GTG GTG CGC TCC AAG CAC CCA CGC      737
Arg Leu Ala His Asn Glu Arg Phe Val Val Arg Ser Lys His Pro Arg
200                 205                 210                 215

AAG GAC GTA GAG TCT GGG TTG TAT CTG ATC GAC CAT CTG AAG AAC CAA      785
Lys Asp Val Glu Ser Gly Leu Tyr Leu Ile Asp His Leu Lys Asn Gln
                220                 225                 230

CCG GAG TTG GGT GGC TAT CAG ATC AGC ATT CCG CAA AAG GGC GTG GTG      833
Pro Glu Leu Gly Gly Tyr Gln Ile Ser Ile Pro Gln Lys Gly Val Val
            235                 240                 245

GAT AAA CGC GGT AAA CGT AAA AAT CGA CCA GCC CGC AAG GCG AGC TTG      881
Asp Lys Arg Gly Lys Arg Lys Asn Arg Pro Ala Arg Lys Ala Ser Leu
        250                 255                 260

AGC CTG CGC AGT GGG CGC ATC ACG CTA AAA CAG GGG AAT ATC ACG CTC      929
Ser Leu Arg Ser Gly Arg Ile Thr Leu Lys Gln Gly Asn Ile Thr Leu
    265                 270                 275

AAC GCG GTG CTG GCC GAG GAG ATT AAC CCG CCC AAG GGT GAG ACC CCG      977
Asn Ala Val Leu Ala Glu Glu Ile Asn Pro Pro Lys Gly Glu Thr Pro
280                 285                 290                 295

TTG AAA TGG TTG TTG CTG ACC GGC GAA CCG GTC GAG TCG CTA GCC CAA     1025
Leu Lys Trp Leu Leu Leu Thr Gly Glu Pro Val Glu Ser Leu Ala Gln
                300                 305                 310

GCC TTG CGC GTC ATC GAC ATT TAT ACC CAT CGC TGG CGG ATC GAG GAG     1073
Ala Leu Arg Val Ile Asp Ile Tyr Thr His Arg Trp Arg Ile Glu Glu
            315                 320                 325

TTC CAT AAG GCA TGG AAA ACC GGA GCA GGA GCC GAG AGG CAA CGC ATG     1121
Phe His Lys Ala Trp Lys Thr Gly Ala Gly Ala Glu Arg Gln Arg Met
        330                 335                 340

GAG GAG CCG GAT AAT CTG GAG CGG ATG GTC TCG ATC CTC TCG TTT GTT     1169
Glu Glu Pro Asp Asn Leu Glu Arg Met Val Ser Ile Leu Ser Phe Val
    345                 350                 355

GCG GTC AGG CTG TTA CAG CTC AGA GAA AGC TTC ACG CCG CCG CAA GCA     1217
Ala Val Arg Leu Leu Gln Leu Arg Glu Ser Phe Thr Pro Pro Gln Ala
360                 365                 370                 375

CTC AGG GCG CAA GGG CTG CTA AAG GAA GCG GAA CAC GTA GAA AGC CAG     1265
Leu Arg Ala Gln Gly Leu Leu Lys Glu Ala Glu His Val Glu Ser Gln
                380                 385                 390

TCC GCA GAA ACG GTG CTG ACC CCG GAT GAA TGT CAG CTA CTG GGC TAT     1313
Ser Ala Glu Thr Val Leu Thr Pro Asp Glu Cys Gln Leu Leu Gly Tyr
            395                 400                 405
```

```
CTG GAC AAG GGA AAA CGC AAG CGC AAA GAG AAA GCA GGT AGC TTG CAG         1361
Leu Asp Lys Gly Lys Arg Lys Arg Lys Glu Lys Ala Gly Ser Leu Gln
        410                 415                 420

TGG GCT TAC ATG GCG ATA GCT AGA CTG GGC GGT TTT ATG GAC AGC AAG         1409
Trp Ala Tyr Met Ala Ile Ala Arg Leu Gly Gly Phe Met Asp Ser Lys
        425                 430                 435

CGA ACC GGA ATT GCC AGC TGG GGC GCC CTC TGG GAA GGT TGG GAA GCC         1457
Arg Thr Gly Ile Ala Ser Trp Gly Ala Leu Trp Glu Gly Trp Glu Ala
440                 445                 450                 455

CTG CAA AGT AAA CTG GAT GGC TTT CTT GCC GCC AAG GAT CTG ATG GCG         1505
Leu Gln Ser Lys Leu Asp Gly Phe Leu Ala Ala Lys Asp Leu Met Ala
        460                 465                 470

CAG GGG ATC AAG ATC TGA TCAAGAGACA G                                    1534
Gln Gly Ile Lys Ile *
        475
```

(2) INFORMATION FOR SEQ ID NO:2:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ile Thr Ser Ala Leu His Arg Ala Ala Asp Trp Ala Lys Ser Val
 1               5                  10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

Ser Ser Glu Gly Ser Lys Ala Ala Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
            85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
        115                 120                 125

Val Leu Leu Leu Glu Ala Thr Thr Phe Arg Thr Val Gly Leu Leu His
    130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
            165                 170                 175

Gly Ser Met Met Ser Asn Val Ile Ala Val Cys Asp Arg Glu Ala Asp
            180                 185                 190

Ile His Ala Tyr Leu Gln Asp Arg Leu Ala His Asn Glu Arg Phe Val
        195                 200                 205

Val Arg Ser Lys His Pro Arg Lys Asp Val Glu Ser Gly Leu Tyr Leu
    210                 215                 220

Ile Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
            245                 250                 255
```

```
Pro Ala Arg Lys Ala Ser Leu Ser Leu Arg Ser Gly Arg Ile Thr Leu
            260                 265                 270
Lys Gln Gly Asn Ile Thr Leu Asn Ala Val Leu Ala Glu Glu Ile Asn
        275                 280                 285
Pro Pro Lys Gly Glu Thr Pro Leu Lys Trp Leu Leu Leu Thr Gly Glu
    290                 295                 300
Pro Val Glu Ser Leu Ala Gln Ala Leu Arg Val Ile Asp Ile Tyr Thr
305                 310                 315                 320
His Arg Trp Arg Ile Glu Glu Phe His Lys Ala Trp Lys Thr Gly Ala
                325                 330                 335
Gly Ala Glu Arg Gln Arg Met Glu Gly Pro Asp Asn Leu Glu Arg Met
            340                 345                 350
Val Ser Ile Leu Ser Phe Val Ala Val Arg Leu Leu Gln Leu Arg Glu
            355                 360                 365
Ser Phe Thr Pro Pro Gln Ala Leu Arg Ala Gln Gly Leu Leu Lys Glu
        370                 375                 380
Ala Glu His Val Glu Ser Gln Ser Ala Glu Thr Val Leu Thr Pro Asp
385                 390                 395                 400
Glu Cys Gln Leu Leu Gly Tyr Leu Asp Lys Gly Lys Arg Lys Arg Lys
                405                 410                 415
Glu Lys Ala Gly Ser Leu Gln Trp Ala Tyr Met Ala Ile Ala Arg Leu
            420                 425                 430
Gly Gly Phe Met Asp Ser Lys Arg Thr Gly Ile Ala Ser Trp Gly Ala
            435                 440                 445
Leu Trp Glu Gly Trp Glu Ala Leu Gln Ser Lys Leu Asp Gly Phe Leu
    450                 455                 460
Ala Ala Lys Asp Leu Met Ala Gln Gly Ile Lys Ile
465                 470                 475

(2) INFORMATION FOR SEQ ID NO:3:

(i) SEQUENCE CHARACTERISTICS:
        (A) LENGTH: 5837 amino acids
        (B) TYPE: nucleic acid
        (C) STRANDEDNESS: double
        (D) TOPOLOGY: circular (ii) MOLECULE TYPE: other nucleic acid
        (A) DESCRIPTION: /desc = "Plasmid DNA"

(vii) IMMEDIATE SOURCE:
        (B) CLONE: pRZTL1

(ix) FEATURE:
        (A) NAME/KEY: insertion_seq
        (B) LOCATION: 1..19

(ix) FEATURE:
        (A) NAME/KEY: CDS
        (B) LOCATION: 77..1267
        (D) OTHER INFORMATION: /function= "tetracycline resistance"

(ix) FEATURE:
        (A) NAME/KEY: CDS
        (B) LOCATION: complement (2301..2960)
        (D) OTHER INFORMATION: /function= "chloramphenicol resistance"

(ix) FEATURE:
        (A) NAME/KEY: insertion_seq
        (B) LOCATION: 4564..4582

(ix) FEATURE:
        (A) NAME/KEY: CDS
        (B) LOCATION: 4715..5530
```

-continued (D) OTHER INFORMATION: /function= "kanamycin resistance"

(xi) SEQUENCE DESCRIPTION: SEQ ID NO:3:

| | | |
|---|---|---|
| CTGACTCTTA TACACAAGTA AGCTTTAATG CGGTAGTTTA TCACAGTTAA ATTGCTAACG | | 60 |
| CAGTCAGGCA CCGTGT ATG AAA TCT AAC AAT GCG CTC ATC GTC ATC CTC | | 109 |
| Met Lys Ser Asn Asn Ala Leu Ile Val Ile Leu | | |
| 480 485 | | |
| GGC ACC GTC ACC CTG GAT GCT GTA GGC ATA GGC TTG GTT ATG CCG GTA | | 157 |
| Gly Thr Val Thr Leu Asp Ala Val Gly Ile Gly Leu Val Met Pro Val | | |
| 490 495 500 | | |
| CTG CCG GGC CTC TTG CGG GAT ATC GTC CAT TCC GAC AGC ATC GCC AGT | | 205 |
| Leu Pro Gly Leu Leu Arg Asp Ile Val His Ser Asp Ser Ile Ala Ser | | |
| 505 510 515 520 | | |
| CAC TAT GGC GTG CTG CTA GCG CTA TAT GCG TTG ATG CAA TTT CTA TGC | | 253 |
| His Tyr Gly Val Leu Leu Ala Leu Tyr Ala Leu Met Gln Phe Leu Cys | | |
| 525 530 535 | | |
| GCA CCC GTT CTC GGA GCA CTG TCC GAC CGC TTT GGC CGC CGC CCA GTC | | 301 |
| Ala Pro Val Leu Gly Ala Leu Ser Asp Arg Phe Gly Arg Arg Pro Val | | |
| 540 545 550 | | |
| CTG CTC GCT TCG CTA CTT GGA GCC ACT ATC GAC TAC GCG ATC ATG GCG | | 349 |
| Leu Leu Ala Ser Leu Leu Gly Ala Thr Ile Asp Tyr Ala Ile Met Ala | | |
| 555 560 565 | | |
| ACC ACA CCC GTC CTG TGG ATC CTC TAC GCC GGA CGC ATC GTG GCC GGC | | 397 |
| Thr Thr Pro Val Leu Trp Ile Leu Tyr Ala Gly Arg Ile Val Ala Gly | | |
| 570 575 580 | | |
| ATC ACC GGC GCC ACA GGT GCG GTT GCT GGC GCC TAT ATC GCC GAC ATC | | 445 |
| Ile Thr Gly Ala Thr Gly Ala Val Ala Gly Ala Tyr Ile Ala Asp Ile | | |
| 585 590 595 600 | | |
| ACC GAT GGG GAA GAT CGG GCT CGC CAC TTC GGG CTC ATG AGC GCT TGT | | 493 |
| Thr Asp Gly Glu Asp Arg Ala Arg His Phe Gly Leu Met Ser Ala Cys | | |
| 605 610 615 | | |
| TTC GGC GTG GGT ATG GTG GCA GGC CCC GTG GCC GGG GGA CTG TTG GGC | | 541 |
| Phe Gly Val Gly Met Val Ala Gly Pro Val Ala Gly Gly Leu Leu Gly | | |
| 620 625 630 | | |
| GCC ATC TCC TTG CAT GCA CCA TTC CTT GCG GCG GCG GTG CTC AAC GGC | | 589 |
| Ala Ile Ser Leu His Ala Pro Phe Leu Ala Ala Ala Val Leu Asn Gly | | |
| 635 640 645 | | |
| CTC AAC CTA CTA CTG GGC TGC TTC CTA ATG CAG GAG TCG CAT AAG GGA | | 637 |
| Leu Asn Leu Leu Leu Gly Cys Phe Leu Met Gln Glu Ser His Lys Gly | | |
| 650 655 660 | | |
| GAG CGT CGA CCG ATG CCC TTG AGA GCC TTC AAC CCA GTC AGC TCC TTC | | 685 |
| Glu Arg Arg Pro Met Pro Leu Arg Ala Phe Asn Pro Val Ser Ser Phe | | |
| 665 670 675 680 | | |
| CGG TGG GCG CGG GGC ATG ACT ATC GTC GCC GCA CTT ATG ACT GTC TTC | | 733 |
| Arg Trp Ala Arg Gly Met Thr Ile Val Ala Ala Leu Met Thr Val Phe | | |
| 685 690 695 | | |
| TTT ATC ATG CAA CTC GTA GGA CAG GTG CCG GCA GCG CTC TGG GTC ATT | | 781 |
| Phe Ile Met Gln Leu Val Gly Gln Val Pro Ala Ala Leu Trp Val Ile | | |
| 700 705 710 | | |
| TTC GGC GAG GAC CGC TTT CGC TGG AGC GCG ACG ATG ATC GGC CTG TCG | | 829 |
| Phe Gly Glu Asp Arg Phe Arg Trp Ser Ala Thr Met Ile Gly Leu Ser | | |
| 715 720 725 | | |
| CTT GCG GTA TTC GGA ATC TTG CAC GCC CTC GCT CAA GCC TTC GTC ACT | | 877 |
| Leu Ala Val Phe Gly Ile Leu His Ala Leu Ala Gln Ala Phe Val Thr | | |
| 730 735 740 | | |
| GGT CCC GCC ACC AAA CGT TTC GGC GAG AAG CAG GCC ATT ATC GCC GGC | | 925 |
| Gly Pro Ala Thr Lys Arg Phe Gly Glu Lys Gln Ala Ile Ile Ala Gly | | |
| 745 750 755 760 | | |
| ATG GCG GCC GAC GCG CTG GGC TAC GTC TTG CTG GCG TTC GCG ACG CGA | | 973 |

```
Met Ala Ala Asp Ala Leu Gly Tyr Val Leu Leu Ala Phe Ala Thr Arg
              765                 770                 775
GGC TGG ATG GCC TTC CCC ATT ATG ATT CTT CTC GCT TCC GGC GGC ATC     1021
Gly Trp Met Ala Phe Pro Ile Met Ile Leu Leu Ala Ser Gly Gly Ile
            780                 785                 790
GGG ATG CCC GCG TTG CAG GCC ATG CTG TCC AGG CAG GTA GAT GAC GAC     1069
Gly Met Pro Ala Leu Gln Ala Met Leu Ser Arg Gln Val Asp Asp Asp
        795                 800                 805
CAT CAG GGA CAG CTT CAA GGA TCG CTC GCG GCT CTT ACC AGC CTA ACT     1117
His Gln Gly Gln Leu Gln Gly Ser Leu Ala Ala Leu Thr Ser Leu Thr
    810                 815                 820
TCG ATC ACT GGA CCG CTG ATC GTC ACG GCG ATT TAT GCC GCC TCG GCG     1165
Ser Ile Thr Gly Pro Leu Ile Val Thr Ala Ile Tyr Ala Ala Ser Ala
825                 830                 835                 840
AGC ACA TGG AAC GGG TTG GCA TGG ATT GTA GGC GCC GCC CTA TAC CTT     1213
Ser Thr Trp Asn Gly Leu Ala Trp Ile Val Gly Ala Ala Leu Tyr Leu
                845                 850                 855
GTC TGC CTC CCC GCG TTG CGT CGC GGT GCA TGG AGC CGG GCC ACC TCG     1261
Val Cys Leu Pro Ala Leu Arg Arg Gly Ala Trp Ser Arg Ala Thr Ser
            860                 865                 870
ACC TGA ATGGAAGCCG CGGCACCTC GCTAACGGAT TCACCACTCC AAGAATTGGA       1317
Thr *
GCCAATCAAT TCTTGCGGAG AACTGTGAAT GCGCAAACCA ACCCTTGGCA GAACATATCC   1377
ATCGCGTCCG CCATCTCCAG CAGCCGCACG CGGCGCATCT CGGGCAGCGT TGGGTCCTGG   1437
CCACGGGTGC GCATGATCGT GCTCCTGTCG TTGAGGACCC GGCTAGGCTG GCGGGGTTGC   1497
CTTACTGGTT AGCAGAATGA ATACCGATA CGCGAGCGAA CGTGAAGCGA CTGCTGCTGC    1557
AAAACGTCTG CGACCTGAGC AACAACATGA ATGGTCTTCG GTTTCCGTGT TTCGTAAAGT   1617
CTGGAAACGC GGAAGTCCCC TACGTGCTGC TGAAGTTGCC CGCAACAGAG AGTGGAACCA   1677
ACCGGTGATA CCACGATACT ATGACTGAGA GTCAACGCCA TGAGCGGCCT CATTTCTTAT   1737
TCTGAGTTAC AACAGTCCGC ACCGCTGTCC GGTAGCTCCT TCCGGTGGGC GCGGGGCATG   1797
ACTATCGTCG CCGCACTTAT GACTGTCTTC TTTATCATGC AACTCGTAGG ACAGGTGCCG   1857
GCAGCGCCCA ACAGTCCCCC GGCCACGGGG CCTGCCACCA TACCCACGCC GAAACAAGCG   1917
CCCTGCACCA TTATGTTCCG GATCTGCATC GCAGGATGCT GCTGGCTACC CTGTGGAACA   1977
CCTACATCTG TATTAACGAA GCGCTAACCG TTTTTATCAG GCTCTGGGAG GCAGAATAAA   2037
TGATCATATC GTCAATTATT ACCTCCACGG GGAGAGCCTG AGCAAACTGG CCTCAGGCAT   2097
TTGAGAAGCA CACGGTCACA CTGCTTCCGG TAGTCAATAA ACCGGTAAAC CAGCAATAGA   2157
CATAAGCGGC TATTTAACGA CCCTGCCCTG AACCGACGAC CGGGTCGAAT TTGCTTTCGA   2217
ATTTCTGCCA TTCATCCGCT TATTATCAAT TATTCAGGCG TAGCACCAGG CGTTTAAGGG   2277
CACCAATAAC TGCCTTAAAA AAATTACGCC CCGCCCTGCC ACTCATCGCA GTACTGTTGT   2337
AATTCATTAA GCATTCTGCC GACATGGAAG CCATCACAGA CGGCATGATG AACCTGAATC   2397
GCCAGCGGCA TCAGCACCTT GTCGCCTTGC GTATAATATT TGCCCATGGT GAAAACGGGG   2457
GCGAAGAAGT TGTCCATATT GGCCACGTTT AAATCAAAAC TGGTGAAACT CACCCAGGGA   2517
TTGGCTGAGA CGAAAAACAT ATTCTCAATA AACCCTTTAG GGAAATAGGC CAGGTTTTCA   2577
CCGTAACACG CCACATCTTG CGAATATATG TGTAGAAACT GCCGGAAATC GTCGTGGTAT   2637
TCACTCCAGA GCGATGAAAA CGTTTCAGTT TGCTCATGGA AAACGGTGTA ACAAGGGTGA   2697
ACACTATCCC ATATCACCAG CTCACCGTCT TTCATTGCCA TACGGAATTC CGGATGAGCA   2757
TTCATCAGGC GGGCAAGAAT GTGAATAAAG GCCGGATAAA ACTTGTGCTT ATTTTTCTTT   2817
```

-continued

```
ACGGTCTTTA AAAAGGCCGT AATATCCAGC TGAACGGTCT GGTTATAGGT ACATTGAGCA    2877

ACTGACTGAA ATGCCTCAAA ATGTTCTTTA CGATGCCATT GGGATATATC AACGGTGGTA    2937

TATCCAGTGA TTTTTTTCTC CATTTTAGCT TCCTTAGCTC CTGAAAATCT CGATAACTCA    2997

AAAAATACGC CCGGTAGTGA TCTTATTTCA TTATGGTGAA AGTTGGAACC TCTTACGTGC    3057

CGATCAACGT CTCATTTTCG CCAAAAGTTG GCCCAGGGCT TCCCGGTATC AACAGGGACA    3117

CCAGGATTTA TTTATTCTGC GAAGTGATCT TCCGTCACAG GTATTTATTC GGCGCAAAGT    3177

GCGTCGGGTG ATGCTGCCAA CTTACTGATT TAGTGTATGA TGGTGTTTTT GAGGTGCTCC    3237

AGTGGCTTCT GTTTCTATCA GCTGTCCCTC CTGTTCAGCT ACTGACGGGG TGGTGCGTAA    3297

CGGCAAAAGC ACCGCCGGAC ATCAGCGCTA GCGGAGTGTA TACTGGCTTA CTATGTTGGC    3357

ACTGATGAGG GTGTCAGTGA AGTGCTTCAT GTGGCAGGAG AAAAAAGGCT GCACCGGTGC    3417

GTCAGCAGAA TATGTGATAC AGGATATATT CCGCTTCCTC GCTCACTGAC TCGCTACGCT    3477

CGGTCGTTCG ACTGCGGCGA GCGGAAATGG CTTACGAACG GGGCGGAGAT TTCCTGGAAG    3537

ATGCCAGGAA GATACTTAAC AGGGAAGTGA GAGGGCCGCG GCAAAGCCGT TTTTCCATAG    3597

GCTCCGCCCC CCTGACAAGC ATCACGAAAT CTGACGCTCA AATCAGTGGT GGCGAAACCC    3657

GACAGGACTA TAAAGATACC AGGCGTTTCC CCTGGCGGCT CCCTCGTGCG CTCTCCTGTT    3717

CCTGCCTTTC GGTTTACCGG TGTCATTCCG CTGTTATGGC CGCGTTTGTC TCATTCCACG    3777

CCTGACACTC AGTTCCGGGT AGGCAGTTCG CTCCAAGCTG GACTGTATGC ACGAACCCCC    3837

CGTTCAGTCC GACCGCTGCG CCTTATCCGG TAACTATCGT CTTGAGTCCA ACCCGGAAAG    3897

ACATGCAAAA GCACCACTGG CAGCAGCCAC TGGTAATTGA TTTAGAGGAG TTAGTCTTGA    3957

AGTCATGCGC CGGTTAAGGC TAAACTGAAA GGACAAGTTT TGGTGACTGC GCTCCTCCAA    4017

GCCAGTTACC TCGGTTCAAA GAGTTGGTAG CTCAGAGAAC CTTCGAAAAA CCGCCCTGCA    4077

AGGCGGTTTT TTCGTTTTCA GAGCAAGAGA TTACGCGCAG ACCAAAACGA TCTCAAGAAG    4137

ATCATCTTAT TAATCAGATA AAATATTTCT AGAGGTGAAC CATCACCCTA ATCAAGTTTT    4197

TTGGGGTCGA GGTGCCGTAA AGCACTAAAT CGGAACCCTA AAGGGATGCC CCGATTTAGA    4257

GCTTGACGGG GAAAGCCGGC GAACGTGGCG AGAAAGGAAG GGAAGAAAGC GAAAGGAGCG    4317

GGCGCTAGGG CGCTGGCAAG TGTAGCGGTC ACGCTGCGCG TAACCACCAC ACCCGCCGCG    4377

CTTAATGCGC CGCTACAGCG CCATTCGCCA TTCAGGCTGC GCAACTGTTG GAAGGGCGA    4437

TCGGTGCGGG CCTCTTCGCT ATTACGCCAG CTGGCGAAAG GGGGATGTGC TGCAAGGCGA    4497

TTAAGTTGGG TAACGCCAGG GTTTTCCCAG TCACGACGTT GTAAAACGAC GGCCAGTGCC    4557

AAGCTTACTT GTGTATAAGA GTCAGTCGAC CTGCAGGGGG GGGGGGAAA GCCACGTTGT    4617

GTCTCAAAAT CTCTGATGTT ACATTGCACA AGATAAAAAT ATATCATCAT GAACAATAAA    4677

ACTGTCTGCT TACATAAACA GTAATACAAG GGGTGTT ATG AGC CAT ATT CAA CGG      4732
                                        Met Ser His Ile Gln Arg
                                          1               5

GAA ACG TCT TGC TCG AGG CCG CGA TTA AAT TCC AAC ATG GAT GCT GAT       4780
Glu Thr Ser Cys Ser Arg Pro Arg Leu Asn Ser Asn Met Asp Ala Asp
         10              15                  20

TTA TAT GGG TAT AAA TGG GCT CGC GAT AAT GTC GGG CAA TCA GGT GCG       4828
Leu Tyr Gly Tyr Lys Trp Ala Arg Asp Asn Val Gly Gln Ser Gly Ala
     25              30                  35

ACA ATC TAT CGA TTG TAT GGG AAG CCC GAT GCG CCA GAG TTG TTT CTG       4876
Thr Ile Tyr Arg Leu Tyr Gly Lys Pro Asp Ala Pro Glu Leu Phe Leu
 40              45              50
```

```
AAA CAT GGC AAA GGT AGC GTT GCC AAT GAT GTT ACA GAT GAG ATG GTC    4924
Lys His Gly Lys Gly Ser Val Ala Asn Asp Val Thr Asp Glu Met Val
 55              60                  65                  70

AGA CTA AAC TGG CTG ACG GAA TTT ATG CCT CTT CCG ACC ATC AAG CAT    4972
Arg Leu Asn Trp Leu Thr Glu Phe Met Pro Leu Pro Thr Ile Lys His
             75                  80                  85

TTT ATC CGT ACT CCT GAT GAT GCA TGG TTA CTC ACC ACT GCG ATC CCC    5020
Phe Ile Arg Thr Pro Asp Asp Ala Trp Leu Leu Thr Thr Ala Ile Pro
                 90                  95                 100

GGG AAA ACA GCA TTC CAG GTA TTA GAA GAA TAT CCT GAT TCA GGT GAA    5068
Gly Lys Thr Ala Phe Gln Val Leu Glu Glu Tyr Pro Asp Ser Gly Glu
            105                 110                 115

AAT ATT GTT GAT GCG CTG GCA GTG TTC CTG CGC CGG TTG CAT TCG ATT    5116
Asn Ile Val Asp Ala Leu Ala Val Phe Leu Arg Arg Leu His Ser Ile
120                 125                 130

CCT GTT TGT AAT TGT CCT TTT AAC AGC GAT CGC GTA TTT CGT CTC GCT    5164
Pro Val Cys Asn Cys Pro Phe Asn Ser Asp Arg Val Phe Arg Leu Ala
135                 140                 145                 150

CAG GCG CAA TCA CGA ATG AAT AAC GGT TTG GTT GAT GCG AGT GAT TTT    5212
Gln Ala Gln Ser Arg Met Asn Asn Gly Leu Val Asp Ala Ser Asp Phe
                155                 160                 165

GAT GAC GAG CGT AAT GGC TGG CCT GTT GAA CAA GTC TGG AAA GAA ATG    5260
Asp Asp Glu Arg Asn Gly Trp Pro Val Glu Gln Val Trp Lys Glu Met
            170                 175                 180

CAT AAG CTT TTG CCA TTC TCA CCG GAT TCA GTC GTC ACT CAT GGT GAT    5308
His Lys Leu Leu Pro Phe Ser Pro Asp Ser Val Val Thr His Gly Asp
                185                 190                 195

TTC TCA CTT GAT AAC CTT ATT TTT GAC GAG GGG AAA TTA ATA GGT TGT    5356
Phe Ser Leu Asp Asn Leu Ile Phe Asp Glu Gly Lys Leu Ile Gly Cys
200                 205                 210

ATT GAT GTT GGA CGA GTC GGA ATC GCA GAC CGA TAC CAG GAT CTT GCC    5404
Ile Asp Val Gly Arg Val Gly Ile Ala Asp Arg Tyr Gln Asp Leu Ala
215                 220                 225                 230

ATC CTA TGG AAC TGC CTC GGT GAG TTT TCT CCT TCA TTA CAG AAA CGG    5452
Ile Leu Trp Asn Cys Leu Gly Glu Phe Ser Pro Ser Leu Gln Lys Arg
                235                 240                 245

CTT TTT CAA AAA TAT GGT ATT GAT AAT CCT GAT ATG AAT AAA TTG CAG    5500
Leu Phe Gln Lys Tyr Gly Ile Asp Asn Pro Asp Met Asn Lys Leu Gln
            250                 255                 260

TTT CAT TTG ATG CTC GAT GAG TTT TTC TAA TCAGAATTGG TTAATTGGTT      5550
Phe His Leu Met Leu Asp Glu Phe Phe *
            265                 270

GTAACACTGG CAGAGCATTA CGCTGACTTG ACGGGACGGC GGCTTTGTTG AATAAATCGA  5610

ACTTTTGCTG AGTTGAAGGA TCAGATCACG CATCTTCCCG ACAACGCAGA CCGTTCCGTG  5670

GCAAAGCAAA AGTTCAAAAT CACCAACTGG TCCACCTACA ACAAAGCTCT CATCAACCGT  5730

GGCTCCCTCA CTTTCTGGCT GGATGATGGG GCGATTCAGG CCTGGTATGA GTCAGCAACA  5790

CCTTCTTCAC GAGGCAGACC TCAGCGCCCC CCCCCCCCTG CAGGTCGA              5838

(2) INFORMATION FOR SEQ ID NO:4:

(i) SEQUENCE CHARACTERISTICS:
        (A) LENGTH: 396 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Ser Asn Asn Ala Leu Ile Val Ile Leu Gly Thr Val Thr Leu
```

```
  1               5               10              15
Asp Ala Val Gly Ile Gly Leu Val Met Pro Val Leu Pro Gly Leu Leu
                20              25              30

Arg Asp Ile Val His Ser Asp Ser Ile Ala Ser His Tyr Gly Val Leu
        35              40              45

Leu Ala Leu Tyr Ala Leu Met Gln Phe Leu Cys Ala Pro Val Leu Gly
    50              55              60

Ala Leu Ser Asp Arg Phe Gly Arg Pro Val Leu Leu Ala Ser Leu
65              70              75              80

Leu Gly Ala Thr Ile Asp Tyr Ala Ile Met Ala Thr Pro Val Leu
                85              90              95

Trp Ile Leu Tyr Ala Gly Arg Ile Val Ala Gly Ile Thr Gly Ala Thr
            100             105             110

Gly Ala Val Ala Gly Ala Tyr Ile Ala Asp Ile Thr Asp Gly Glu Asp
            115             120             125

Arg Ala Arg His Phe Gly Leu Met Ser Ala Cys Phe Gly Val Gly Met
    130             135             140

Val Ala Gly Pro Val Ala Gly Gly Leu Leu Gly Ala Ile Ser Leu His
145             150             155             160

Ala Pro Phe Leu Ala Ala Val Leu Asn Gly Leu Asn Leu Leu
            165             170             175

Gly Cys Phe Leu Met Gln Glu Ser His Lys Gly Glu Arg Arg Pro Met
            180             185             190

Pro Leu Arg Ala Phe Asn Pro Val Ser Ser Phe Arg Trp Ala Arg Gly
        195             200             205

Met Thr Ile Val Ala Ala Leu Met Thr Val Phe Phe Ile Met Gln Leu
    210             215             220

Val Gly Gln Val Pro Ala Ala Leu Trp Val Ile Phe Gly Glu Asp Arg
225             230             235             240

Phe Arg Trp Ser Ala Thr Met Ile Gly Leu Ser Leu Ala Val Phe Gly
            245             250             255

Ile Leu His Ala Leu Ala Gln Ala Phe Val Thr Gly Pro Ala Thr Lys
            260             265             270

Arg Phe Gly Glu Lys Gln Ala Ile Ile Ala Gly Met Ala Ala Asp Ala
        275             280             285

Leu Gly Tyr Val Leu Leu Ala Phe Ala Thr Arg Gly Trp Met Ala Phe
    290             295             300

Pro Ile Met Ile Leu Leu Ala Ser Gly Gly Ile Gly Met Pro Ala Leu
305             310             315             320

Gln Ala Met Leu Ser Arg Gln Val Asp Asp His Gln Gly Gln Leu
            325             330             335

Gln Gly Ser Leu Ala Ala Leu Thr Ser Leu Thr Ser Ile Thr Gly Pro
            340             345             350

Leu Ile Val Thr Ala Ile Tyr Ala Ala Ser Ala Ser Thr Trp Asn Gly
            355             360             365

Leu Ala Trp Ile Val Gly Ala Leu Tyr Leu Val Cys Leu Pro Ala
        370             375             380

Leu Arg Arg Gly Ala Trp Ser Arg Ala Thr Ser Thr
385             390             395
```

(2) INFORMATION FOR SEQ ID NO:5:

(i) SEQUENCE CHARACTERISTICS:
        (A) LENGTH: 219 amino acids (B) TYPE: amino acid
      (D) TOPOLOGY: linear (ii) MOLECULE TYPE: protein (xi) SEQUENCE DESCRIPTION: SEQ ID NO:5:

Met Glu Lys Lys Ile Thr Gly Tyr Thr Thr Val Asp Ile Ser Gln Trp
 1               5                  10                  15

His Arg Lys Glu His Phe Glu Ala Phe Gln Ser Val Ala Gln Cys Thr
             20                  25                  30

Tyr Asn Gln Thr Val Gln Leu Asp Ile Thr Ala Phe Leu Lys Thr Val
         35                  40                  45

Lys Lys Asn Lys His Lys Phe Tyr Pro Ala Phe Ile His Ile Leu Ala
     50                  55                  60

Arg Leu Met Asn Ala His Pro Glu Phe Arg Met Ala Met Lys Asp Gly
 65                  70                  75                  80

Glu Leu Val Ile Trp Asp Ser Val His Pro Cys Tyr Thr Val Phe His
                 85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215                 220

(2) INFORMATION FOR SEQ ID NO:6:

(i) SEQUENCE CHARACTERISTICS:
      (A) LENGTH: 271 amino acids
      (B) TYPE: amino acid
      (D) TOPOLOGY: linear (ii) MOLECULE TYPE: protein (xi) SEQUENCE DESCRIPTION: SEQ ID NO:6:

Met Ser His Ile Gln Arg Glu Thr Ser Cys Ser Arg Pro Arg Leu Asn
 1               5                  10                  15

Ser Asn Met Asp Ala Asp Leu Tyr Gly Tyr Lys Trp Ala Arg Asp Asn
             20                  25                  30

Val Gly Gln Ser Gly Ala Thr Ile Tyr Arg Leu Tyr Gly Lys Pro Asp
         35                  40                  45

Ala Pro Glu Leu Phe Leu Lys His Gly Lys Gly Ser Val Ala Asn Asp
     50                  55                  60

Val Thr Asp Glu Met Val Arg Leu Asn Trp Leu Thr Glu Phe Met Pro
 65                  70                  75                  80

Leu Pro Thr Ile Lys His Phe Ile Arg Thr Pro Asp Asp Ala Trp Leu
                 85                  90                  95

```
Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
            115                 120                 125

Arg Arg Leu His Ser Ile Pro Val Cys Asn Cys Pro Phe Asn Ser Asp
            130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
            195                 200                 205

Gly Lys Leu Ile Gly Cys Ile Asp Val Gly Arg Val Gly Ile Ala Asp
            210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
                260                 265                 270

(2) INFORMATION FOR SEQ ID NO:7:

(i) SEQUENCE CHARACTERISTICS:
        (A) LENGTH: 18 amino acids
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Tn5 wild type outside end"

(xi) SEQUENCE DESCRIPTION: SEQ ID NO:7:

CTGACTCTTA TACACAAGT                                            19

(2) INFORMATION FOR SEQ ID NO:8:

(i) SEQUENCE CHARACTERISTICS:
        (A) LENGTH: 18 amino acids
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Tn5 mutant outside end"

(xi) SEQUENCE DESCRIPTION: SEQ ID NO:8:

CTGTCTCTTA TACACATCT                                            19

(2) INFORMATION FOR SEQ ID NO:9:

(i) SEQUENCE CHARACTERISTICS:
        (A) LENGTH: 18 amino acids
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Tn5 mutant outside end"

(xi) SEQUENCE DESCRIPTION: SEQ ID NO:9:
```

```
CTGTCTCTTA TACAGATCT                                                    19
```

(2) INFORMATION FOR SEQ ID NO:10:

(i) SEQUENCE CHARACTERISTICS:
        (A) LENGTH: 18 amino acids
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Tn5 wild type inside end"

(xi) SEQUENCE DESCRIPTION: SEQ ID NO:10:

```
CTGTCTCTTG ATCAGATCT                                                    19
```

(2) INFORMATION FOR SEQ ID NO:11:

(i) SEQUENCE CHARACTERISTICS:
        (A) LENGTH: 19181 amino acids
        (B) TYPE: nucleic acid
        (C) STRANDEDNESS: double
        (D) TOPOLOGY: circular (ii) MOLECULE TYPE: other nucleic acid
        (A) DESCRIPTION: /desc = "Plasmid pRZ4196"

(ix) FEATURE:
        (A) NAME/KEY: repeat_unit
        (B) LOCATION: 94..112
        (D) OTHER INFORMATION: /note= "Wild type OE sequence"

(ix) FEATURE:
        (A) NAME/KEY: repeat_unit
        (B) LOCATION: 12184..12225
        (D) OTHER INFORMATION: /note= "Cassette IE"

(xi) SEQUENCE DESCRIPTION: SEQ ID NO:11:

```
TTCCTGTAAC AATAGCAATA CCCCAAATAC CTAATGTAGT TCCAGCAAGC AAGCTAAAAA        60

GTAAAGCAAC AACATAACTC ACCCCTGCAT CTGCTGACTC TTATACACAA GTAGCGTCCC       120

GGGATCGGGA TCCCGTCGTT TTACAACGTC GTGACTGGGA AAACCCTGGC GTTACCCAAC       180

TTAATCGCCT TGCAGCACAT CCCCCTTTCG CCAGCTGGCG TAATAGCGAA GAGGCCCGCA       240

CCGATCGCCC TTCCCAACAG TTGCGCAGCC TGAATGGCGA ATGGCGCTTT GCCTGGTTTC       300

CGGCACCAGA AGCGGTGCCG GAAAGCTGGC TGGAGTGCGA TCTTCCTGAG GCCGATACTG       360

TCGTCGTCCC CTCAAACTGG CAGATGCACG GTTACGATGC GCCCATCTAC ACCAACGTAA       420

CCTATCCCAT TACGGTCAAT CCGCCGTTTG TTCCCACGGA GAATCCGACG GGTTGTTACT       480

CGCTCACATT TAATGTTGAT GAAAGCTGGC TACAGGAAGG CCAGACGCGA ATTATTTTTG       540

ATGGCGTTAA CTCGGCGTTT CATCTGTGGT GCAACGGGCG CTGGGTCGGT TACGGCCAGG       600

ACAGTCGTTT GCCGTCTGAA TTTGACCTGA GCGCATTTTT ACGCGCCGGA GAAAACCGCC       660

TCGCGGTGAT GGTGCTGCGT TGGAGTGACG GCAGTTATCT GGAAGATCAG GATATGTGGC       720

GGATGAGCGG CATTTTCCGT GACGTCTCGT TGCTGCATAA ACCGACTACA CAAATCAGCG       780

ATTTCCATGT TGCCACTCGC TTTAATGATG ATTTCAGCCG CGCTGTACTG GAGGCTGAAG       840

TTCAGATGTG CGGCGAGTTG CGTGACTACC TACGGGTAAC AGTTTCTTTA TGGCAGGGTG       900

AAACGCAGGT CGCCAGCGGC ACCGCGCCTT TCGGCGGTGA AATTATCGAT GAGCGTGGTG       960

GTTATGCCGA TCGCGTCACA CTACGTCTGA ACGTCGAAAA CCCGAAACTG TGGAGCGCCG      1020

AAATCCCGAA TCTCTATCGT GCGGTGGTTG AACTGCACAC CGCCGACGGC ACGCTGATTG      1080

AAGCAGAAGC CTGCGATGTC GGTTTCCGCG AGGTGCGGAT TGAAAATGGT CTGCTGCTGC      1140
```

```
                                              -continued

TGAACGGCAA GCCGTTGCTG ATTCGAGGCG TTAACCGTCA CGAGCATCAT CCTCTGCATG    1200

GTCAGGTCAT GGATGAGCAG ACGATGGTGC AGGATATCCT GCTGATGAAG CAGAACAACT    1260

TTAACGCCGT GCGCTGTTCG CATTATCCGA ACCATCCGCT GTGGTACACG CTGTGCGACC    1320

GCTACGGCCT GTATGTGGTG GATGAAGCCA ATATTGAAAC CCACGGCATG GTGCCAATGA    1380

ATCGTCTGAC CGATGATCCG CGCTGGCTAC CGGCGATGAG CGAACGCGTA ACGCGAATGG    1440

TGCAGCGCGA TCGTAATCAC CCGAGTGTGA TCATCTGGTC GCTGGGGAAT GAATCAGGCC    1500

ACGGCGCTAA TCACGACGCG CTGTATCGCT GGATCAAATC TGTCGATCCT TCCCGCCCGG    1560

TGCAGTATGA AGGCGGCGGA GCCGACACCA CGGCCACCGA TATTATTTGC CCGATGTACG    1620

CGCGCGTGGA TGAAGACCAG CCCTTCCCGG CTGTGCCGAA ATGGTCCATC AAAAAATGGC    1680

TTTCGCTACC TGGAGAGACG CGCCCGCTGA TCCTTTGCGA ATACGCCCAC GCGATGGGTA    1740

ACAGTCTTGG CGGTTTCGCT AAATACTGGC AGGCGTTTCG TCAGTATCCC CGTTTACAGG    1800

GCGGCTTCGT CTGGGACTGG GTGGATCAGT CGCTGATTAA ATATGATGAA ACGGCAACC    1860

CGTGGTCGGC TTACGGCGGT GATTTTGGCG ATACGCCGAA CGATCGCCAG TTCTGTATGA    1920

ACGGTCTGGT CTTTGCCGAC CGCACGCCGC ATCCAGCGCT GACGGAAGCA AAACACCAGC    1980

AGCAGTTTTT CCAGTTCCGT TTATCCGGGC AAACCATCGA AGTGACCAGC GAATACCTGT    2040

TCCGTCATAG CGATAACGAG CTCCTGCACT GGATGGTGGC GCTGGATGGT AAGCCGCTGG    2100

CAAGCGGTGA AGTGCCTCTG GATGTCGCTC ACAAGGTAA ACAGTTGATT GAACTGCCTG    2160

AACTACCGCA GCCGGAGAGC GCCGGGCAAC TCTGGCTCAC AGTACGCGTA GTGCAACCGA    2220

ACGCGACCGC ATGGTCAGAA GCCGGGCACA TCAGCGCCTG GCAGCAGTGG CGTCTGGCGG    2280

AAAACCTCAG TGTGACGCTC CCCGCCGCGT CCCACGCCAT CCCGCATCTG ACCACCAGCG    2340

AAATGGATTT TTGCATCGAG CTGGGTAATA AGCGTTGGCA ATTTAACCGC CAGTCAGGCT    2400

TTCTTTCACA GATGTGGATT GGCGATAAAA ACAACTGCT GACGCCGCTG CGCGATCAGT    2460

TCACCCGTGC ACCGCTGGAT AACGACATTG GCGTAAGTGA AGCGACCCGC ATTGACCCTA    2520

ACGCCTGGGT CGAACGCTGG AAGGCGGCGG GCCATTACCA GGCCGAAGCA GCGTTGTTGC    2580

AGTGCACGGC AGATACACTT GCTGATGCGG TGCTGATTAC GACCGCTCAC GCGTGGCAGC    2640

ATCAGGGGAA AACCTTATTT ATCAGCCGGA AAACCTACCG GATTGATGGT AGTGGTCAAA    2700

TGGCGATTAC CGTTGATGTT GAAGTGGCGA GCGATACACC GCATCCGGCG CGGATTGGCC    2760

TGAACTGCCA GCTGGCGCAG GTAGCAGAGC GGGTAAACTG GCTCGGATTA GGGCCGCAAG    2820

AAAACTATCC CGACCGCCTT ACTGCCGCCT GTTTTGACCG CTGGGATCTG CCATTGTCAG    2880

ACATGTATAC CCCGTACGTC TTCCCGAGCG AAAACGGTCT GCGCTGCGGG ACGCGCGAAT    2940

TGAATTATGG CCCACACCAG TGGCGCGGCG ACTTCCAGTT CAACATCAGC CGCTACAGTC    3000

AACAGCAACT GATGGAAACC AGCCATCGCC ATCTGCTGCA CGCGGAAGAA GGCACATGGC    3060

TGAATATCGA CGGTTTCCAT ATGGGGATTG GTGGCGACGA CTCCTGGAGC CCGTCAGTAT    3120

CGGCGGATTC CAGCTGAGCG CCGGTCGCTA CCATTACCAG TTGGTCTGGT GTCAAAATA    3180

ATAATAACCG GGCAGGCCAT GTCTGCCCGT ATTTCGCGTA AGGAAATCCA TTATGTACTA    3240

TTTAAAAAAC ACAAACTTTT GGATGTTCGG TTTATTCTTT TTCTTTTACT TTTTTATCAT    3300

GGGAGCCTAC TTCCCGTTTT TCCCGATTTG GCTACATGAC ATCAACCATA TCAGCAAAAG    3360

TGATACGGGT ATTATTTTTG CCGCTATTTC TCTGTTCTCG CTATTATTCC AACCGCTGTT    3420

TGGTCTGCTT TCTGACAAAC TCGGGCTGCG CAAATACCTG CTGTGGATTA TTACCGGCAT    3480
```

```
GTTAGTGATG TTTGCGCCGT TCTTTATTTT TATCTTCGGG CCACTGTTAC AATACAACAT    3540

TTTAGTAGGA TCGATTGTTG GTGGTATTTA TCTAGGCTTT TGTTTTAACG CCGGTGCGCC    3600

AGCAGTAGAG GCATTTATTG AGAAAGTCAG CCGTCGCAGT AATTTCGAAT TTGGTCGCGC    3660

GCGGATGTTT GGCTGTGTTG GCTGGGCGCT GTGTGCCTCG ATTGTCGGCA TCATGTTCAC    3720

CATCAATAAT CAGTTTGTTT TCTGGCTGGG CTCTGGCTGT GCACTCATCC TCGCCGTTTT    3780

ACTCTTTTTC GCCAAAACGG ATGCGCCCTC TTCTGCCACG GTTGCCAATG CGGTAGGTGC    3840

CAACCATTCG GCATTTAGCC TTAAGCTGGC ACTGGAACTG TTCAGACAGC CAAAACTGTG    3900

GTTTTTGTCA CTGTATGTTA TTGGCGTTTC CTGCACCTAC GATGTTTTTG ACCAACAGTT    3960

TGCTAATTTC TTTACTTCGT TCTTTGCTAC CGGTGAACAG GGTACGCGGG TATTTGGCTA    4020

CGTAACGACA ATGGGCGAAT TACTTAACGC CTCGATTATG TTCTTTGCGC CACTGATCAT    4080

TAATCGCATC GGTGGGAAAA ACGCCCTGCT GCTGGCTGGC ACTATTATGT CTGTACGTAT    4140

TATTGGCTCA TCGTTCGCCA CCTCAGCGCT GGAAGTGGTT ATTCTGAAAA CGCTGCATAT    4200

GTTTGAAGTA CCGTTCCTGC TGGTGGGCTG CTTTAAATAT ATTACCAGCC AGTTTGAAGT    4260

GCGTTTTTCA GCGACGATTT ATCTGGTCTG TTTCTGCTTC TTTAAGCAAC TGGCGATGAT    4320

TTTTATGTCT GTACTGGCGG GCAATATGTA TGAAAGCATC GGTTTCCAGG GCGCTTATCT    4380

GGTGCTGGGT CTGGTGGCGC TGGGCTTCAC CTTAATTTCC GTGTTCACGC TTAGCGGCCC    4440

CGGCCCGCTT TCCCTGCTGC GTCGTCAGGT GAATGAAGTC GCTTAAGCAA TCAATGTCGG    4500

ATGCGGCGCG ACGCTTATCC GACCAACATA TCATAACGGA GTGATCGCAT TGAACATGCC    4560

AATGACCGAA AGAATAAGAG CAGGCAAGCT ATTTACCGAT ATGTGCGAAG GCTTACCGGA    4620

AAAAAGACTT CGTGGGAAAA CGTTAATGTA TGAGTTTAAT CACTCGCATC CATCAGAAGT    4680

TGAAAAAAGA GAAAGCCTGA TTAAAGAAAT GTTTGCCACG GTAGGGGAAA ACGCCTGGGT    4740

AGAACCGCCT GTCTATTTCT CTTACGGTTC CAACATCCAT ATAGGCCGCA ATTTTTATGC    4800

AAATTTCAAT TTAACCATTG TCGATGACTA CACGGTAACA ATCGGTGATA ACGTACTGAT    4860

TGCACCCAAC GTTACTCTTT CCGTTACGGG ACACCCTGTA CACCATGAAT TGAGAAAAAA    4920

CGGCGAGATG TACTCTTTTC CGATAACGAT TGGCAATAAC GTCTGGATCG GAAGTCATGT    4980

GGTTATTAAT CCAGGCGTCA CCATCGGGGA TAATTCTGTT ATTGGCGCGG GTAGTATCGT    5040

CACAAAAGAC ATTCCACCAA ACGTCGTGGC GGCTGGCGTT CCTTGTCGGG TTATTCGCGA    5100

AATAAACGAC CGGGATAAGC ACTATTATTT CAAAGATTAT AAAGTTGAAT CGTCAGTTTA    5160

AATTATAAAA ATTGCCTGAT ACGCTGCGCT TATCAGGCCT ACAAGTTCAG CGATCTACAT    5220

TAGCCGCATC CGGCATGAAC AAAGCGCAGG AACAAGCGTC GCATCATGCC TCTTTGACCC    5280

ACAGCTGCGG AAAACGTACT GGTGCAAAAC GCAGGGTTAT GATCATCAGC CAACGACGC    5340

ACAGCGCATG AAATGCCCAG TCCATCAGGT AATTGCCGCT GATACTACGC AGCACGCCAG    5400

AAAACCACGG GGCAAGCCCG GCGATGATAA AACCGATTCC CTGCATAAAC GCCACCAGCT    5460

TGCCAGCAAT AGCCGGTTGC ACAGAGTGAT CGAGCGCCAG CAGCAAACAG AGCGGAAACG    5520

CGCCGCCCAG ACCTAACCCA CACACCATCG CCCACAATAC CGGCAATTGC ATCGGCAGCC    5580

AGATAAAGCC GCAGAACCCC ACCAGTTGTA ACACCAGCGC CAGCATTAAC AGTTTGCGCC    5640

GATCCTGATG GCGAGCCATA GCAGGCATCA GCAAAGCTCC TGCGGCTTGC CCAAGCGTCA    5700

TCAATGCCAG TAAGGAACCG CTGTACTGCG CGCTGGCACC AATCTCAATA TAGAAAGCGG    5760

GTAACCAGGC AATCAGGCTG GCGTAACCGC CGTTAATCAG ACCGAAGTAA ACACCCAGCG    5820

TCCACGCGCG GGGAGTGAAT ACCACGCGAA CCGGAGTGGT TGTTGTCTTG TGGGAAGAGG    5880
```

```
CGACCTCGCG GGCGCTTTGC CACCACCAGG CAAAGAGCGC AACAACGGCA GGCAGCGCCA   5940

CCAGGCGAGT GTTTGATACC AGGTTTCGCT ATGTTGAACT AACCAGGGCG TTATGGCGGC   6000

ACCAAGCCCA CCGCCGCCCA TCAGAGCCGC GGACCACAGC CCCATCACCA GTGGCGTGCG   6060

CTGCTGAAAC CGCCGTTTAA TCACCGAAGC ATCACCGCCT GAATGATGCC GATCCCCACC   6120

CCACCAAGCA GTGCGCTGCT AAGCAGCAGC GCACTTTGCG GGTAAAGCTC ACGCATCAAT   6180

GCACCGACGG CAATCAGCAA CAGACTGATG GCGACACTGC GACGTTCGCT GACATGCTGA   6240

TGAAGCCAGC TTCCGGCCAG CGCCAGCCCG CCCATGGTAA CCACCGGCAG AGCGGTCGAC   6300

CCGGACGGGA CGCTCCTGCG CCTGATACAG AACGAATTGC TTGCAGGCAT CTCATGAGTG   6360

TGTCTTCCCG TTTTCCGCCT GAGGTCACTG CGTGGATGGA GCGCTGGCGC CTGCTGCGCG   6420

ACGGCGAGCT GCTCACCACC CACTCGAGCT GGATACTTCC CGTCCGCCAG GGGACATGC    6480

CGGCGATGCT GAAGGTCGCG CGCATTCCCG ATGAAGAGGC CGGTTACCGC CTGTTGACCT   6540

GGTGGGACGG GCAGGGCGCC GCCCGAGTCT TCGCCTCGGC GGCGGGCGCT CTGCTCATGG   6600

AGCGCGCGTC CGGGGCCGGG GACCTTGCAC AGATAGCGTG GTCCGGCCAG GACGACGAGG   6660

CTTGCAGGAT CTATGATTCC CTTTGTCAAC AGCAATGGAT CACTGAAAAT GGTTCAATGA   6720

TCACATTAAG TGGTATTCAA TATTTTCATG AAATGGGAAT TGACGTTCCT TCCAAACATT   6780

CACGTAAAAT CTGTTGTGCG TGTTTAGATT GGAGTGAACG CCGTTTCCAT TTAGGTGGGT   6840

ACGTTGGAGC CGCATTATTT TCGCTTTATG AATCTAAAGG GTGGTTAACT CGACATCTTG   6900

GTTACCGTGA AGTTACCATC ACGGAAAAAG GTTATGCTGC TTTTAAGACC CACTTTCACA   6960

TTTAAGTTGT TTTTCTAATC CGCATATGAT CAATTCAAGG CCGAATAAGA AGGCTGGCTC   7020

TGCACCTTGG TGATCAAATA ATTCGATAGC TTGTCGTAAT AATGGCGGCA TACTATCAGT   7080

AGTAGGTGTT TCCCTTTCTT CTTTAGCGAC TTGATGCTCT TGATCTTCCA ATACGCAACC   7140

TAAAGTAAAA TGCCCCACAG CGCTGAGTGC ATATAATGCA TTCTCTAGTG AAAAACCTTG   7200

TTGGCATAAA AAGGCTAATT GATTTTCGAG AGTTTCATAC TGTTTTTCTG TAGGCCGTGT   7260

ACCTAAATGT ACTTTTGCTC CATCGCGATG ACTTAGTAAA GCACATCTAA AACTTTTAGC   7320

GTTATTACGT AAAAAATCTT GCCAGCTTTC CCCTTCTAAA GGGCAAAAGT GAGTATGGTG   7380

CCTATCTAAC ATCTCAATGG CTAAGGCGTC GAGCAAAGCC CGCTTATTTT TTACATGCCA   7440

ATACAATGTA GGCTGCTCTA CACCTAGCTT CTGGGCGAGT TTACGGGTTG TTAAACCTTC   7500

GATTCCGACC TCATTAAGCA GCTCTAATGC GCTGTTAATC ACTTTACTTT TATCTAATCT   7560

AGACATCATT AATTCCTAAT TTTTGTTGAC ACTCTATCAT TGATAGAGTT ATTTTACCAC   7620

TCCCTATCAG TGATAGAGAA AAGTGAAATG AATAGTTCGA CAAAGATCGC ATTGGTAATT   7680

ACGTTACTCG ATGCCATGGG GATTGGCCTT ATCATGCCAG TCTTGCCAAC GTTATTACGT   7740

GAATTTATTG CTTCGGAAGA TATCGCTAAC CACTTTGGCG TATTGCTTGC ACTTTATGCG   7800

TTAATGCAGG TTATCTTTGC TCCTTGGCTT GGAAAAATGT CTGACCGATT TGGTCGGCGC   7860

CCAGTGCTGT TGTTGTCATT AATAGGCGCA TCGCTGGATT ACTTATTGCT GGCTTTTTCA   7920

AGTGCGCTTT GGATGCTGTA TTTAGGCCGT TTGCTTTCAG GGATCACAGG AGCTACTGGG   7980

GCTGTCGCGG CATCGGTCAT TGCCGATACC ACCTCAGCTT CTCAACGCGT GAAGTGGTTC   8040

GGTTGGTTAG GGGCAAGTTT TGGGCTTGGT TTAATAGCGG GGCCTATTAT TGGTGGTTTT   8100

GCAGGAGAGA TTTCACCGCA TAGTCCCTTT TTTATCGCTG CGTTGCTAAA TATTGTCACT   8160

TTCCTTGTGG TTATGTTTTG GTTCCGTGAA ACCAAAAATA CACGTGATAA TACAGATACC   8220
```

-continued

| | | | | | |
|---|---|---|---|---|---|
| GAAGTAGGGG | TTGAGACGCA | ATCGAATTCG | GTATACATCA | CTTTATTTAA | AACGATGCCC | 8280 |
| ATTTTGTTGA | TTATTTATTT | TTCAGCGCAA | TTGATAGGCC | AAAATTCCCGC | AACGGTGTGG | 8340 |
| GTGCTATTTA | CCGAAAATCG | TTTTGGATGG | AATAGCATGA | TGGTTGGCTT | TTCATTAGCG | 8400 |
| GGTCTTGGTC | TTTTACACTC | AGTATTCCAA | GCCTTTGTGG | CAGGAAGAAT | AGCCACTAAA | 8460 |
| TGGGGCGAAA | AAACGGCAGT | ACTGCTCGAA | TTTATTGCAG | ATAGTAGTGC | ATTTGCCTTT | 8520 |
| TTAGCGTTTA | TATCTGAAGG | TTGGTTAGAT | TTCCCTGTTT | TAATTTTATT | GGCTGGTGGT | 8580 |
| GGGATCGCTT | TACCTGCATT | ACAGGGAGTG | ATGTCTATCC | AAACAAAGAG | TCATGAGCAA | 8640 |
| GGTGCTTTAC | AGGGATTATT | GGTGAGCCTT | ACCAATGCAA | CCGGTGTTAT | TGGCCCATTA | 8700 |
| CTGTTTACTG | TTATTTATAA | TCATTCACTA | CCAATTTGGG | ATGGCTGGAT | TTGGATTATT | 8760 |
| GGTTTAGCGT | TTTACTGTAT | TATTATCCTG | CTATCGATGA | CCTTCATGTT | AACCCCTCAA | 8820 |
| GCTCAGGGGA | GTAAACAGGA | GACAAGTGCT | TAGTTATTTC | GTCACCAAAT | GATGTTATTC | 8880 |
| CGCGAAATAT | AATGACCCTC | TTGATAACCC | AAGAGGGCAT | TTTTTACGAT | AAAGAAGATT | 8940 |
| TAGCTTCAAA | TAAAACCTAT | CTATTTTATT | TATCTTTCAA | GCTCAATAAA | AAGCCGCGGT | 9000 |
| AAATAGCAAT | AAATTGGCCT | TTTTTATCGG | CAAGCTCTTT | TAGGTTTTTC | GCATGTATTG | 9060 |
| CGATATGCAT | AAACCAGCCA | TTGAGTAAGT | TTTTAAGCAC | ATCACTATCA | TAAGCTTTAA | 9120 |
| GTTGGTTCTC | TTGGATCAAT | TTGCTGACAA | TGGCGTTTAC | CTTACCAGTA | ATGTATTCAA | 9180 |
| GGCTAATTTT | TTCAAGTTCA | TTCCAACCAA | TGATAGGCAT | CACTTCTTGG | ATAGGGATAA | 9240 |
| GGTTTTTATT | ATTATCAATA | ATATAATCAA | GATAATGTTC | AAATATACTT | TCTAAGGCAG | 9300 |
| ACCAACCATT | TGTTAAATCA | GTTTTTGTTG | TGATGTAGGC | ATCAATCATA | ATTAATTGCT | 9360 |
| GCTTATAACA | GGCACTGAGT | AATTGTTTTT | TATTTTAAA | GTGATGATAA | AAGGCACCTT | 9420 |
| TGGTCACCAA | CGCTTTTCCC | GAGATCCTCT | GCGACACCGC | CGCTCGTCTG | CACGCGCCGC | 9480 |
| GGTCCGGACC | GCCGCCCGAT | CTCCATCCGC | TACAGGAATG | GTTCCAGCCG | CTTTTCCGGT | 9540 |
| TGGCCGCTGA | GCACGCGGCA | CTTGCGCCCG | CCGCCAGCGT | AGCGCGCCAA | CTTCTGGCGG | 9600 |
| CGCCGCGCGA | GGTGTGCCCG | CTCCACGGCG | ACCTGCACCA | CGAGAACGTG | CTCGACTTCG | 9660 |
| GCGACCGCGG | CTGGCTGGCC | ATCGACCCGC | ACGGACTGCT | CGGCGAGCGC | ACCTTCGACT | 9720 |
| ATGCCAACAT | CTTCACGAAT | CCCGATCTCA | GCGACCCCGG | TCGCCCGCTT | GCGATCCTGC | 9780 |
| CGGGCAGGCT | GGAGGCTCGA | CTCAGCATTG | TGGTCGCGAC | GACCGGGTTT | GAGCCCGAAC | 9840 |
| GGCTTCTTCG | CTGGATCATT | GCATGGACGG | GCTTGTCGGC | AGCCTGGTTC | ATCGGCGACG | 9900 |
| GCGACGGCGA | GGGCGAGGGC | GCTGCGATTG | ATCTGGCCGT | AAACGCCATG | GCACGCCGGT | 9960 |
| TGCTTGACTA | GCGCGGTCAC | CGATCTCACC | TGGTCGTCGA | GCTAGGTCAG | GCCGTGTCGG | 10020 |
| GCGTGATCCG | CTGGAAGTCG | TTGCGGGCCA | CACCCGCCGC | CTCGAAGCCC | TGCACCAGGC | 10080 |
| CGGCATCGTG | GTGTGCGTGG | CCGAGGGACT | ATGGAAGGTG | CCGGACGATC | TGCCCGAGCA | 10140 |
| GGGCCGCCGC | TATGACGCCC | AGCGTCTTGG | TGGCGTGACG | GTGGAGCTGA | AATCGCACCT | 10200 |
| GCCCATCGAG | CGGCAGGCCC | GCGTGATCGG | TGCCACCTGG | CTTGACCAGC | AGTTGATCGA | 10260 |
| CGGTGGCTCG | GGCTTGGGCG | ACCTGGGCTT | TAGCAGTGAG | GCCAAGTAGG | CGATACAGCA | 10320 |
| GCGCGCGGAC | TTCCTGGCCG | AACAGGGACT | GGCCGAGCGG | CGCGGGCAGC | GCGTGATCCT | 10380 |
| CACCGGAATC | TGCTGGGCAG | CAGCGGGCTC | GGGAACTGGC | GCAGGCCGCG | AAGGACATTG | 10440 |
| CCGCCGATAC | CGGCCTGGAG | CATCGCCCCG | TGGCCGACGG | CCAGCGCGTT | GCCGGCGTCT | 10500 |
| ACCGGCGCCC | CGTCATGCTC | GCCAGCGGGC | GAAATGGGAT | GCTTGATGAC | GCCAAGGGGT | 10560 |
| CCAGCCTCGT | GCGGTGGAAG | CCCATCGAAC | AGCGGCTTGG | GGAGCAGCTC | GCCGCGACGG | 10620 |

-continued

```
TGCGCGGTGG CGGCGTGTCT TGGGAGATTG GACGACAGCG TGGGCCGGCC CCTGTCTCTT    10680

GATCAGATCT TGATCCCCTG CGCCATCAGA TCCTTGGCGG CAAGAAAGCC ATCCAGTTTA    10740

CTTTGCAGGG CTTCCCAACC TTCCCAGAGG GCGCCCCAGC TGGCAATTCC GGTTCGCTTG    10800

CTGTCCATAA AACCGCCCAG TCTAGCTATC GCCATGTAAG CCCACTGCAA GCTACCTGCT    10860

TTCTCTTTGC GCTTGCGTTT TCCCTTGTCC AGATAGCCCA GTAGCTGACA TTCATCCGGG    10920

GTCAGCACCG TTTCTGCGGA CTGGCTTTCT ACGTGTTCCG CTTCCTTTAG CAGCCCTTGC    10980

GCCCTGAGTG CTTGCGGCAG CGTGAAGCTT TCTCTGAGCT GTAACAGCCT GACCGCAACA    11040

AACGAGAGGA TCGAGACCAT CCGCTCCAGA TTATCCGGCT CCTCCATGCG TTGCCTCTCG    11100

GCTCCTGCTC CGGTTTTCCA TGCCTTATGG AACTCCTCGA TCCGCCAGCG ATGGGTATAA    11160

ATGTCGATGA CGCGCAAGGC TTGGGCTAGC GACTCGACCG GTTCGCCGGT CAGCAACAAC    11220

CATTTCAACG GGGTCTCACC CTTGGGCGGG TTAATCTCCT CGGCCAGCAC CGCGTTGAGC    11280

GTGATATTCC CCTGTTTTAG CGTGATGCGC CCACTGCGCA GGCTCAAGCT CGCCTTGCGG    11340

GCTGGTCGAT TTTTACGTTT ACCGCGTTTA TCCACCACGC CCTTTTGCGG AATGCTGATC    11400

TGATAGCCAC CCAACTCCGG TTGGTTCTTC AGATGGTCGA TCAGATACAA CCCAGACTCT    11460

ACGTCCTTGC GTGGGTGCTT GGAGCGCACC ACGAAGCGCT CGTTATGCGC CAGCCTGTCC    11520

TGCAGATAAG CATGAATATC GGCTTCGCGG TCACAGACCG CAATCACGTT GCTCATCATG    11580

CTGCCCATGC GTAACCGGCT AGTTGCGGCC GCTGCCAGCC ATTTGCCACT CTCCTTTTCA    11640

TCCGCATCGG CAGGGTCATC CGGGCGCATC CACCACTCCT GATGCAGTAA TCCTACGGTG    11700

CGGAATGTGG TGGCCTCGAG CAAGAGAACG GAGTGAACCC ACCATCCGCG GGATTTATCC    11760

TGAATAGAGC CCAGCTTGCC AAGCTCTTCG GCGACCTGGT GGCGATAACT CAAAGAGGTG    11820

GTGTCCTCAA TGGCCAGCAG TTCGGGAAAC TCCTGAGCCA ACTTGACTGT TTGCATGGCG    11880

CCAGCCTTTC TGATCGCCTC GGCAGAAACG TTGGGATTGC GGATAAATCG GTAAGCGCCT    11940

TCCTGCATGG CTTCACTACC CTCTGATGAG ATGGTTATTG ATTTACCAGA ATATTTTGCC    12000

AATTGGGCGG CGACGTTAAC CAAGCGGGCA GTACGGCGAG GATCACCCAG CGCCGCCGAA    12060

GAGAACACAG ATTTAGCCCA GTCGGCCGCA CGATGAAGAG CAGAAGTTAT CATGAACGTT    12120

ACCATGTTAG GAGGTCACAT GGAAGATCAG ATCCTGGAAA ACGGGAAAGG TTCCGTTCGA    12180

ATTGCATGCG GATCCGGGAT CAAGATCTGA TCAAGAGACA GGTACCAATT GTTGAAGACG    12240

AAAGGGCCTC GTGATACGCC TATTTTTATA GGTTAATGTC ATGATAATAA TGGTTTCTTA    12300

GACGTCAGGT GGCACTTTTC GGGGAAATGT GCGCGGAACC CCTATTTGTT TATTTTTCTA    12360

AATACATTCA AATATGTATC CGCTCATGAG ACAATAACCC TGATAAATGC TTCAATAATA    12420

TTGAAAAAGG AAGAGTATGA GTATTCAACA TTTCCGTGTC GCCCTTATTC CCTTTTTTGC    12480

GGCATTTTGC CTTCCTGTTT TTGCTCACCC AGAAACGCTG GTGAAAGTAA AAGATGCTGA    12540

AGATCAGTTG GGTGCACGAG TGGGTTACAT CGAACTGGAT CTCAACAGCG GTAAGATCCT    12600

TGAGAGTTTT CGCCCCGAAG AACGTTTTCC AATGATGAGC ACTTTTAAAG TTCTGCTATG    12660

TGGCGCGGTA TTATCCCGTG TTGACGCCGG GCAAGAGCAA CTCGGTCGCC GCATACACTA    12720

TTCTCAGAAT GACTTGGTTG AGTACTTGGC AAACTGATCT AAATGTTTAG CCCAGTCATC    12780

ATACTTCACC GATGCCAACG CATTAAAAAT AGCATCACGA TCGGCTTTGC TGAATTTCTT    12840

ATTTAAAACA TCCTTGTATT TTTCAAAAGC AGCGAGAGCT TCATTCACAT TGCCGATTTT    12900

CTTACCTTTA GACTTATCAG CAAGTTCCTG TGCCATTTTC GAATATTTTT CACCATATTT    12960
```

```
                                                            -continued
TTCAGTCAGC GTTTGATAAA AGCTAACTGT TGCATCAACA GCATCCTTAA TCTGTGAATT    13020

AAGGAGATTA TTCTGTGCTT TTTTCAAATT TTCTTCAGCT TCATGAACAC GAGCGATACC    13080

GGCATTACGA TTATTACTGA CCTGAGAAAT AGCCTTCTGG ATCTGAGTTA TATCAGCATT    13140

TATCCGGTTA ATACGTGTTT CTGATGCTGT TACCTGTTTT TGTTTTTCTT CTCTAATCTT    13200

ACCGGCCCCA ACCCGTCGTC TGGTTGCTTC AAAAAAAGGA CGGTTCTGAA GCGGATCATT    13260

GGCTCTTGGT GATAGTTTTT TGACCAGCTC ATCCAGTTCT TTATATTTAG CGGATGCCTG    13320

AGCCAGTTCA TTTCGTTTTC CAGCGAGCGT TTTCATTTCT GCATCACGGG CATGGATACT    13380

GGAGCTTAAA CGAGAATTGA GAGTCTTAAT CTCTCCATCC ATTTTCACCA CTTCAGATTG    13440

TGCAGCAGAA AGTTTTTTTT GGGCGATCTC AACAGCTTTA GCTTCTTCAC TCAATGCAGC    13500

CAGTCGTTTC TCTTCAGCTT CAGCCAGTTT CAACTGGCGT TCTGTTTCAG CCTTCTCCCG    13560

TTCAATCTCT TTACGTCGTT GTTCTGCTTC CTGAAAAGCC TTTTCTGCTG CTTCCGCTTC    13620

TTTACGGGCT TTTTCTTCTG CTTTCGCAAG GCGCAAACGC TCTGCTTCCG CCTGCATAGC    13680

TGCATTATTA GCATGAGCAA GCTCTGTTGC TGAAGGCGTA CGTGAGGCAT TGTGACGAAG    13740

AGCCTCATTC ACGATATCCT TCAGGCGCTG AGTCAGCGCA TCCCTGTTTG CCTTTGCTTT    13800

CGCCTGTGCT TCCGCTGCAG CTTTTGCCCG GGCAGCCTGC TCTGCCTGTG TTTTCTTTAA    13860

TTGAGCAGTA GACCATTTAG CAGTTGCATG AATAGCTGCA GAACTTTCAC TTTTACTGCC    13920

TCCTTTTCCA CCTCCGCCGC CAGAGCCACT CCCGTCAGGA GTACCATTCA AAAGAGTAAT    13980

AATTACCTGT CCCTTATCAT CATAAGGAAC ACCATCTTTA TAGTACGCTA CCGCGGTTTC    14040

CATTATAAAA TCCTCTTTGA CTTTTAAAAC AATAAGTTAA AAATAAATAC TGTACATATA    14100

ACCACTGGTT TTATATACAG CATAAAAGCT ACGCCGCTGC ATTTTCCCTG TCAAGACTGT    14160

GGACTTCCAT TTTTGTGAAA ACGATCAAAA AAACAGTCTT TCACACCACG CGCTATTCTC    14220

GCCCGATGCC ACAAAAACCA GCACAAACAT TACCGTTCTC AGACCTCATT ATGTTTTACT    14280

GAAACTATGA GATGAGACAT CTATGGGACA CTGTCACTTT ATGGCATGGC ACACACTCCG    14340

GGACGCACTA AAAATGACAG GCAGATCGCG TTCACAGTTT TACCGTGATA TGCGCGGAGG    14400

CCTTGTCAGT TACCGTACCG GCAGGGACGG ACGACGGGAG TTTGAAACCA GTGAACTGAT    14460

CCGGGCATAC GGCGAATTAA AGCAGAATGA GACACCAGAA AGGCACAGTG AGGGACATGC    14520

AGAAAATCCA CATGATCAGC AGACAGAACG CATTCTCCGG GAACTGAATG AGCTGAAACA    14580

ATGCCTGACG CTGATGCTTG AGGATAAACA GGCACAGGAT ATGGATCGCA GACGCCAGGA    14640

AGCAGAACGG GAACAGCTAC AAAATGAGAT AGCCCAGCTC AGGCAGGCAC TGGAACTGGA    14700

AAAGAAACGG GGATTCTGGT CCAGGTTGTT CGGTCGCTGA ACGCTGTCAG AGACTGATGA    14760

TAAAATAGTC TTCGGATAAT AACTCACCGA GAATAAATAC TTTAAGGTAG GGAGACACTC    14820

ATGAGACGTA CCGGAAACAA ACTTTGTCTT ATCGCCATGA TAACAGCAAC AGTAGCTCTC    14880

ACAGCCTGTA CCCCAAAGGG CAGCGTGGAA CAACATACCC GGCATTACGT ATATGCTTCT    14940

GATGACGGTT TTGATCCCAA CTTTTCCACC CAAAAAGCCG ACACAACACG AATGATGGTG    15000

CCTTTTTTTC GGCAGTTCTG GGATATGGGA GCTAAAGACA AAGCGACAGG AAAATCACGG    15060

AGTGATGTGC AACAACGCAT TCAGCAGTTT CACAGCCAAG AATTTTTAAA CTCACTCCGG    15120

GGCACAACTC AATTTGCGGG TACTGATTAC CGCAGCAAAG ACCTTACCCC GAAAAAATCC    15180

AGGCTGCTGG CTGACACGAT TTCTGCGGTT TATCTCGATG GCTACGAGGG CAGACAGTAA    15240

GTGGATTTAC CATAATCCCT TAATTGTACG CACCGCTAAA ACGCGTTCAG CGCGATCACG    15300

GCAGCAGACA GGTAAAAATG GCAACAAACC ACCCTAAAAA CTGCGCGATC GCGCCTGATA    15360
```

-continued

```
AATTTTAACC GTATGAATAC CTATGCAACC AGAGGGTACA GGCCACATTA CCCCCACTTA    15420

ATCCACTGAA GCTGCCATTT TTCATGGTTT CACCATCCCA GCGAAGGGCC ATCCAGCGTG    15480

CGTTCCTGTA TTTCCGGCTG ACGCTCCCGT TCTAGGGATA ACACATGTTC GCGCTCCTGT    15540

ATCAGCCGTT CCTCTCTTAT CTCCAGTTCT CGCTGTATAA CTGGCTCAAG CGTTCTGTCT    15600

GCTCGCTCAA GTGTTGCACC TGCTGACTCA ACTGCATGAC CCGCTCGTTC AGCATCGCGT    15660

TGTCCCGTTG CGTAAGCGAA AACATCTTCT GCAATTCCAC GAAGGCGCTC TCCCATTCGC    15720

TCAGCCGCTG CATATAGTCC TGTTGCAGCT GCTCTAAGGC GTTCAGCAAA TGTGTTTCCA    15780

GCTCTGTCAC TCTGTGTCAC TCCTTCAGAT GTACCCACTC TTTCCCCTGA AAGGGAATCA    15840

CCTCCGCTGA TTTCCCGTAC GGAAGGACAA GGAATTTCCT GTTCCCGTCC TGCACAAACT    15900

CCACGCCCCA TGTCTTCGCG TTCAGTTTCT GCAATGTCTC TTCCTGCTTC CTGATTTCTT    15960

CCAGGTTCGC CTGTATCCTC CCTCCAAGAT ACCAGAGCGT CCCGCCACTC GCGGTAAACA    16020

GGAGAAAGAC TATCCCCAGT AACATCATGC CCGTATTCCC TGCCAGCTTT AACACGTCCC    16080

TCCTGTGCTG CATCATCGCC TCTTTCACCC CTTCCCGGTG TTTTTCCAGC GATTCCTCTG    16140

TCGAGGCTGT GAACAGGGCT ATAGCGTCTC TGATTTTCGT CTCGTTTGAT GTCACAGCCT    16200

CGCTTACAGA TTCGCCGAGC CTCCTGAACT CGTTGTTCAG CATTTTCTCT GTAGATTCGG    16260

CTCTCTCTTT CAGCTTTTTC TCGAACTCCG CGCCCGTCTG CAAAAGATTG CTCATAAAAT    16320

GCTCCTTTCA GCCTGATATT CTTCCCGCCG TTCGGATCTG CAATGCTGAT ACTGCTTCGC    16380

GTCACCCTGA CCACTTCCAG CCCCGCCTCA GTGAGCGCCT GAATCACATC CTGACGGCCT    16440

TTTATCTCTC CGGCATGGTA AAGTGCATCT ATACCTCGCG TGACGCCCTC AGCAAGCGCC    16500

TGTTTCGTTT CAGGCAGGTT ATCAGGGAGT GTCAGCGTCC TGCGGTTCTC CGGGGCGTTC    16560

GGGTCATGCA GCCCGTAATG GTGATTTAAC AGCGTCTGCC AAGCATCAAT TCTAGGCCTG    16620

TCTGCGCGGT CGTAGTACGG CTGGAGGCGT TTTCCGGTCT GTAGCTCCAT GTTCGGAATG    16680

ACAAAATTCA GCTCAAGCCG TCCCTTGTCC TGGTGCTCCA CCCACAGGAT GCTGTACTGA    16740

TTTTTTTCGA GACCGGGCAT CAGTACACGC TCAAAGCTCG CCATCACTTT TTCACGTCCT    16800

CCCGGCGGCA GCTCCTTCTC CGCGAACGAC AGAACACCGG ACGTGTATTT CTTCGCAAAT    16860

GGCGTGGCAT CGATGAGTTC CCGGACTTCT TCCGGTATAC CCTGAAGCAC CGTTGCGCCT    16920

TCGCGGTTAC GCTCCCTCCC CAGCAGGTAA TCAACCGGAC CACTGCCACC ACCTTTTCCC    16980

CTGGCATGAA ATTTAACTAT CATCCCGCGC CCCCTGTTCC CTGACAGCCA GACGCAGCCG    17040

GCGCAGCTCA TCCCCGATGG CCATCAGTGC GGCCACCACC TGAACCCGGT CACCGGAAGA    17100

CCACTGCCCG CTGTTCACCT TACGGGCTGT CTGATTCAGG TTATTTCCGA TGGCGGCCAG    17160

CTGACGCAGT AACGGCGGTG CCAGTGTCGG CAGTTTTCCG GAACGGGCAA CCGGCTCCCC    17220

CAGGCAGACC CGCCGCATCC ATACCGCCAG TTGTTTACCC TCACAGCGTT CAAGTAACCG    17280

GGCATGTTCA TCATCAGTAA CCCGTATTGT GAGCATCCTC TCGCGTTTCA TCGGTATCAT    17340

TACCCCATGA ACAGAAATCC CCCTTACACG GAGGCATCAG TGACTAAACA GGAAAAAACC    17400

GCCCTTAACA TGGCCCGCTT TATCAGAAGC CAGACATTAA CGCTGCTGGA GAAGCTCAAC    17460

GAACTGGACG CAGATGAACA GGCCGATATT TGTGAATCGC TTCACGACCA CGCCGATGAG    17520

CTTTACCGCA GCTGCCTCGC ACGTTTCGGG GATGACGGTG AAAACCTCTG ACACATGCAG    17580

CTCCCGGAGA CGGTCACAGC TTGTCTGTGA GCGGATGCCG GGAGCTGACA AGCCCGTCAG    17640

GGCGCGTCAG CAGGTTTTAG CGGGTGTCGG GGCGCAGCCC TGACCCAGTC ACGTAGCGAT    17700
```

-continued

```
AGCGGAGTGT ATACTGGCTT AACCATGCGG CATCAGTGCG GATTGTATGA AAAGTACGCC     17760

ATGCCGGGTG TGAAATGCCG CACAGATGCG TAAGGAGAAA ATGCACGTCC AGGCGCTTTT     17820

CCGCTTCCTC GCTCACTGAC TCGCTACGCT CGGTCGTTCG ACTGCGGCGA GCGGTACTGA     17880

CTCACACAAA AACGGTAACA CAGTTATCCA CAGAATCAGG GGATAAGGCC GGAAAGAACA     17940

TGTGAGCAAA AGACCAGGAA CAGGAAGAAG GCCACGTAGC AGGCGTTTTT CCATAGGCTC     18000

CGCCCCCCTG ACGAGCATCA CAAAAATAGA CGCTCAAGTC AGAGGTGGCG AAACCCGACA     18060

GGACTATAAA GCTACCAGGC GTTTCCCCCT GGAAGCTCCC TCGTGCGCTC TCCTGTTCCG     18120

ACCCTGCCGC TTACCGGATA CCTGTCCGCC TTTCTCCCTT CGGGAAGCGT GGCGCTTTCT     18180

CATAGCTCAC GCTGTTGGTA TCTCAGTTCG GTGTAGGTCG TTCGCTCCAA GCTGGGCTGT     18240

GTGCACGAAC CCCCCGTTCA GCCCGACCGC TGCGCCTTAT CCGGTAACTA TCGTCTTGAG     18300

TCCAACCCGG TAAGGCACGC CTTAACGCCA CTGGCAGCAG CCACTGGTAA CCGGATTAGC     18360

AGAGCGATGA TGGCACAAAC GGTGCTACAG AGTTCTTGAA GTAGTGGCCC GACTACGGCT     18420

ACACTAGAAG GACAGTATTT GGTATCTGCG CTCTGCTGAA GCCAGTTACC TTCGGAAAAA     18480

GAGTTGGTAG CTCTTGATCC GGCAAACAAA CCACCGTTGG TAGCGGTGGT TTTTTTGTTT     18540

GCAAGCAGCA GATTACGCGC AGAAAAAAAG GATCTCAAGA AGATCCTTTA ATCTTTTCTA     18600

CTGAACCGCG ATCCCCGTCA GTTTAGAAGA GGAGGATGGT GCGATGGTCC CTCCCTGAAC     18660

ATCAGGTATA TAGTTAGCCT GACATCCAAC AAGGAGGTTT ATCGCGAATA TTCCCACAAA     18720

AAATCTTTTC CTCATAACTC GATCCTTATA AAATGAAAAG AATATATGGC GAGGTTTAAT     18780

TTATGAGCTT AAGATACTAC ATAAAAAATA TTTTATTTGG CCTGTACTGC ACACTTATAT     18840

ATATATACCT TATAACAAAA AACAGCGAAG GGTATTATTT CCTTGTGTCA GATAAGATGC     18900

TATATGCAAT AGTGATAAGC ACTATTCTAT GTCCATATTC AAAATATGCT ATTGAATACA     18960

TAGCTTTTAA CTTCATAAAG AAAGATTTTT TCGAAAGAAG AAAAAACCTA AATAACGCCC     19020

CCGTAGCAAA ATTAAACCTA TTTATGCTAT ATAATCTACT TTGTTTGGTC CTAGCAATCC     19080

CATTTGGATT GCTAGGACTT TTTATATCAA TAAAGAATAA TTAAATCCCT AACACCTCAT     19140

TTATAGTATT AAGTTTATTC TTATCAATAT AGGAGCATAG AA                       19182
```

SYSTEM FOR *IN VITRO* TRANSPOSITION

CROSS-REFERENCE TO RELATED APPLICATION

This patent application is a divisional of application Ser. No. 08/850,880 filed May 2, 1997 now U.S. Pat. No. 5,925,545 which was a continuation-in-part of application Ser. No. 08/814,877 filed Sep. 9, 1996 now U.S. Pat. No. 5,965,443.

STATEMENT REGARDING FEDERALLY SPONSORED RESEARCH OR DEVELOPMENT

This invention was made with U.S. government support awarded by the following agencies:
NIH Grant No.: GM50692
NSF Grant No.: MCB-9419784
The United States has certain rights in this invention.

BACKGROUND OF THE INVENTION

The present invention relates generally to the field of transposable nucleic acid and, more particularly to production and use of a modified transposase enzyme in a system for introducing genetic changes to nucleic acid.

Transposable genetic elements are DNA sequences, found in a wide variety of prokaryotic and eukaryotic organisms, that can move or transpose from one position to another position in a genome. In vivo, intra-chromosomal transpositions as well as transpositions between chromosomal and non-chromosomal genetic material are known. In several systems, transposition is known to be under the control of a transposase enzyme that is typically encoded by the transposable element. The genetic structures and transposition mechanisms of various transposable elements are summarized, for example, in "Transposable Genetic Elements" in "The Encyclopedia of Molecular Biology," Kendrew and Lawrence, Eds., Blackwell Science, Ltd., Oxford (1994), incorporated herein by reference.

In vitro transposition systems that utilize the particular transposable elements of bacteriophage Mu and bacterial transposon Tn10 have been described, by the research groups of Kiyoshi Mizuuchi and Nancy Kleckner, respectively.

The bacteriophage Mu system was first described by Mizuuchi, K., "In Vitro Transposition of Bacteria Phage Mu: A Biochemical Approach to a Novel Replication Reaction," *Cell*:785–794 (1983) and Craigie, R. et al., "A Defined System for the DNA Strand-Transfer Reaction at the Initiation of Bacteriophage Mu Transposition: Protein and DNA Substrate Requirements," *P.N.A.S. U.S.A.* 82:7570–7574 (1985). The DNA donor substrate (mini-Mu) for Mu in vitro reaction normally requires six Mu transposase binding sites (three of about 30 bp at each end) and an enhancer sequence located about 1 kb from the left end. The donor plasmid must be supercoiled. Proteins required are Mu-encoded A and B proteins and host-encoded HU and IHF proteins. Lavoie, B.D, and G. Chaconas, "Transposition of phage Mu DNA," *Curr. Topics Microbiol. Immunol.* 204:83–99 (1995). The Mu-based system is disfavored for in vitro transposition system applications because the Mu termini are complex and sophisticated and because transposition requires additional proteins above and beyond the transposase.

The Tn10 system was described by Morisato, D. and N. Kleckner, "Tn10 Transposition and Circle Formation in vitro," *Cell* 51:101–111 (1987) and by Benjamin, H. W. and N. Kleckner, "Excision Of Tn10 from the Donor Site During Transposition Occurs By Flush Double-Strand Cleavages at the Transposon Termini," *P.N.A.S. U.S.A.* 89:4648–4652 (1992). The Tn10 system involves the a supercoiled circular DNA molecule carrying the transposable element (or a linear DNA molecule plus *E. coli* IHF protein). The transposable element is defined by complex 42 bp terminal sequences with IHF binding site adjacent to the inverted repeat. In fact, even longer (81 bp) ends of Tn10 were used in reported experiments. Sakai, J. et al., "Identification and Characterization of Pre-Cleavage Synaptic Complex that is an Early Intermediate in Tn10 transposition," *E.M.B.O. J.* 14:4374–4383 (1995). In the Tn10 system, chemical treatment of the transposase protein is essential to support active transposition. In addition, the termini of the Tn10 element limit its utility in a generalized in vitro transposition system.

Both the Mu-and Tn10-based in vitro transposition systems are further limited in that they are active only on covalently closed circular, supercoiled DNA targets. What is desired is a more broadly applicable in. vitro transposition system that utilizes shorter, more well defined termini and which is active on target DNA of any structure (linear, relaxed circular, and supercoiled circular DNA).

BRIEF SUMMARY OF THE INVENTION

The present invention is summarized in that an in vitro transposition system comprises a preparation of a suitably modified transposase of bacterial transposon Tn5, a donor DNA molecule that includes a transposable element, a target DNA molecule into which the transposable element can transpose, all provided in a suitable reaction buffer.

The transposable element of the donor DNA molecule is characterized as a transposable DNA sequence of interest, the DNA sequence of interest being flanked at its 5'- and 3'-ends by short repeat sequences that are acted upon in trans by Tn5 transposase.

The invention is further summarized in that the suitably modified transposase enzyme comprises two classes of differences from wild type Tn5 transposase, where each class has a separate measurable effect upon the overall transposition activity of the enzyme and where a greater effect is observed when both modifications are present. The suitably modified enzyme both (1) binds to the repeat sequences of the donor DNA with greater avidity than wild type Tn5 transposase ("class (1) mutation") and (2) is less likely than the wild type protein to assume an inactive multimeric form ("class (2) mutation"). A suitably modified Tn5 transposase of the present invention that contains both class (1) and class (2) modifications induces at least about 100-fold (±10%) more transposition than the wild type enzyme, when tested in combination in an in vivo conjugation assay as described by Weinreich, M. D., "Evidence that the cis Preference of the Tn5 Transposase is Caused by Nonproductive Multimerization," *Genes and Development* 8:2363–2374 (1994), incorporated herein by reference. Under optimal conditions, transposition using the modified transposase may be higher. A modified transposase containing only a class (1) mutation binds to the repeat sequences with sufficiently greater avidity than the wild type Tn5 transposase that such a Tn5 transposase induces about 5- to 50-fold more transposition than the wild type enzyme, when measured in vivo. A modified transposase containing only a class (2) mutation is sufficiently less likely than the wild type Tn5 transposase to assume the multimeric form that such a Tn5 transposase also induces about 5- to 50-fold more transposition than the wild type enzyme, when measured in vivo.

In another aspect, the invention is summarized in that a method for transposing the transposable element from the donor DNA into the target DNA in vitro includes the steps of mixing together the suitably modified Tn5 transposase protein, the donor DNA, and the target DNA in a suitable reaction buffer, allowing the enzyme to bind to the flanking repeat sequences of the donor DNA at a temperature greater than 0° C., but no higher than about 28° C., and then raising the temperature to physiological temperature (about 37° C.) whereupon cleavage and strand transfer can occur.

It is an object of the present invention to provide a useful in vitro transposition system having few structural requirements and high efficiency.

It is another object of the present invention to provide a method that can be broadly applied in various ways, such as to create absolute defective mutants, to provide selective markers to target DNA, to provide portable regions of homology to a target DNA, to facilitate insertion of specialized DNA sequences into target DNA, to provide primer binding sites or tags for DNA sequencing, to facilitate production of genetic fusions for gene expression studies and protein domain mapping, as well as to bring together other desired combinations of DNA sequences (combinatorial genetics).

It is a feature of the present invention that the modified transposase enzyme binds more tightly to DNA than does wild type Tn5 transposase.

It is an advantage of the present invention that the modified transposase facilitates in vitro transposition reaction rates of at least about 100-fold higher than can be achieved using wild type transposase (as measured in vivo). It is noted that the wild-type Tn5 transposase shows no detectable in vitro activity in the system of the present invention. Thus, while it is difficult to calculate an upper limit to the increase in activity, it is clear that hundreds, if not thousands, of colonies are observed when the products of in vitro transposition are assayed in vivo.

It is another advantage of the present invention that in vitro transposition using this system can utilize donor DNA and target DNA that is circular or linear.

It is yet another advantage of the present invention that in vitro transposition using this system requires no outside high energy source and no other protein other than the modified transposase.

Other objects, features, and advantages of the present invention will become apparent upon consideration of the following detailed description.

DETAILED DESCRIPTION OF THE INVENTION

Figure 1:
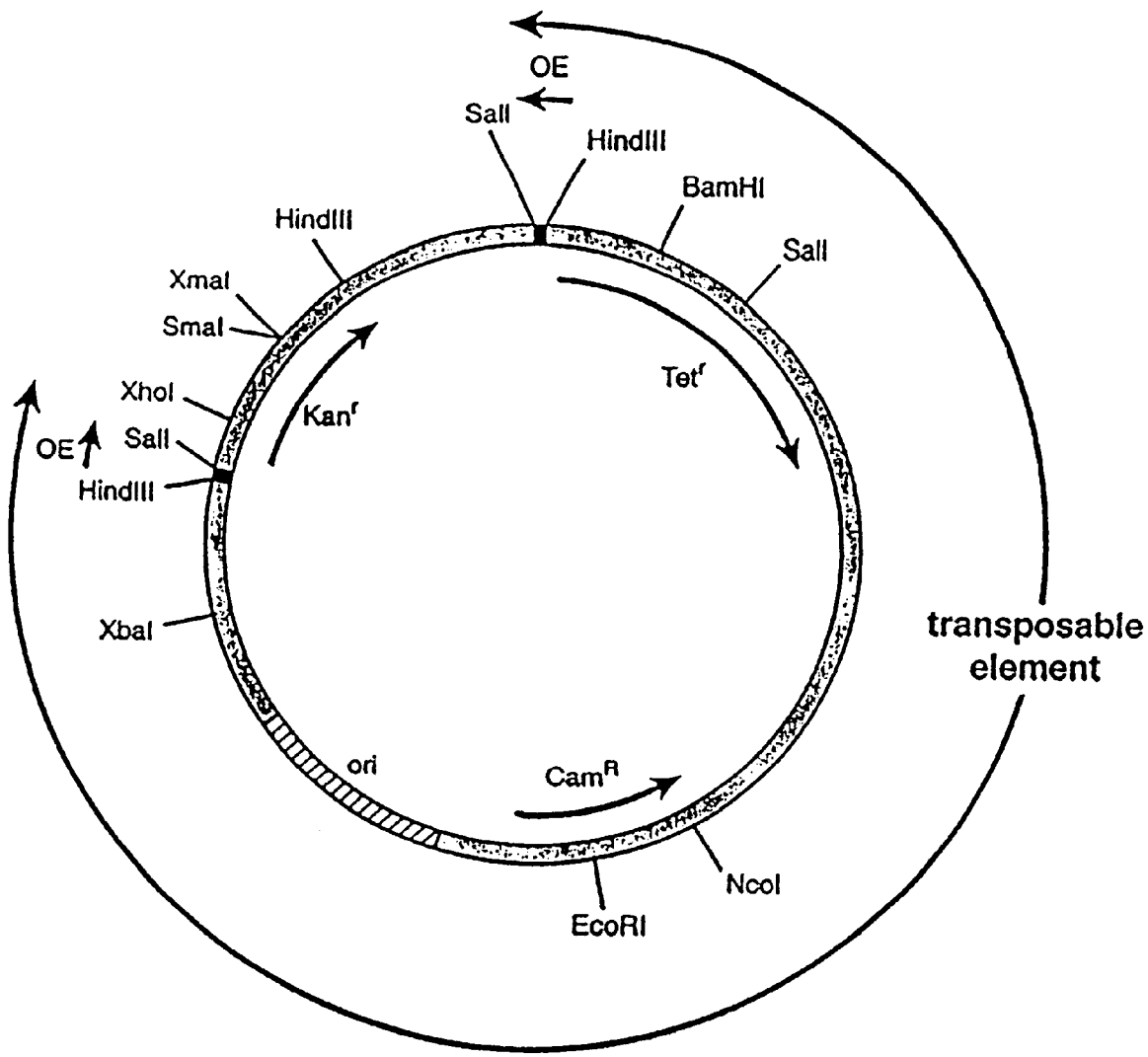
FIG. 1 depicts test plasmid pRZTL1, used herein to demonstrate transposition in vitro of a transposable element located between a pair of Tn5 outside end termini. Plasmid pRZTL1 is also shown and described in SEQ ID NO:3.

It will be appreciated that this technique provides a simple, in vitro system for introducing any transposable element from a donor DNA into a target DNA. It is generally accepted and understood that Tn5 transposition requires only a pair of OE termini, located to either side of the transposable element. These OE termini are generally thought to be 18 or 19 bases in length and are inverted repeats relative to one another. Johnson, R. C., and W. S. Reznikoff, Nature 304:280 (1983), incorporated herein by reference. The Tn5 inverted repeat sequences, which are referred to as "termini" even though they need not be at the termini of the donor DNA molecule, are well known and understood.

Apart from the need to flank the desired transposable element with standard Tn5 outside end ("OE") termini, few other requirements on either the donor DNA or the target DNA are envisioned. It is thought that Tn5 has few, if any, preferences for insertion sites, so it is possible to use the system to introduce desired sequences at random into target DNA. Therefore, it is believed that this method, employing the modified transposase described herein and a simple donor DNA, is broadly applicable to introduce changes into any target DNA, without regard to its nucleotide sequence. It will, thus, be applied to many problems of interest to those skilled in the art of molecular biology.

In the method, the modified transposase protein is combined in a suitable reaction buffer with the donor DNA and the target DNA. A suitable reaction buffer permits the transposition reaction to occur. A preferred, but not necessarily optimized, buffer contains spermidine to condense the DNA, glutamate, and magnesium, as well as a detergent, which is preferably 3-[(3-cholamidopropyl) dimethyl-ammonio]-1-propane sulfonate ("CHAPS"). The mixture can be incubated at a temperature greater than 0° C. and as high as about 28° C. to facilitate binding of the enzyme to the OE termini. Under the buffer conditions used by the inventors in the Examples, a pretreatment temperature of 30° C. was not adequate. A preferred temperature range is between 16° C. and 28° C. A most preferred pretreatment temperature is about 20° C. Under different buffer conditions, however, it may be possible to use other below-physiological temperatures for the binding step. After a short pretreatment period of time (which has not been optimized, but which may be as little as 30 minutes or as much as 2 hours, and is typically 1 hour), the reaction mixture is diluted with 2 volumes of a suitable reaction buffer and shifted to physiological conditions for several more hours (say 2–3 hours) to permit cleavage and strand transfer to occur. A temperature of 37° C., or thereabouts, is adequate. After about 3 hours, the rate of transposition decreases markedly. The reaction can be stopped by phenol-chloroform extraction and can then be desalted by ethanol precipitation.

When the DNA has been purified using conventional purification tools, it is possible to employ simpler reaction conditions in the in vitro transposition method. DNA of sufficiently high purity can be prepared by passing the DNA preparation through a resin of the type now commonly used in the molecular biology laboratory, such as the Qiagen resin of the Qiagen plasmid purification kit (Catalog No. 12162). When such higher quality DNA is employed, CHAPS can be omitted from the reaction buffer. When CHAPS is eliminated from the reaction buffer, the reactants need not be diluted in the manner described above. Also, the low temperature incubation step noted above can be eliminated in favor of a single incubation for cleavage and strand transfer at physiological conditions. A three hour incubation at 37° C. is sufficient.

Following the reaction and subsequent extraction steps, transposition can be assayed by introducing the nucleic acid reaction products into suitable bacterial host cells (e.g., *E. coli* K-12 DH5α cells (recA⁻); commercially available from Life Technologies (Gibco-BRL)) preferably by electroporation, described by Dower et al., *Nuc. Acids. Res.* 16:6127 (1988), and monitoring for evidence of transposition, as is described elsewhere herein.

Those persons skilled in the art will appreciate that apart from the changes noted herein, the transposition reaction can proceed under much the same conditions as would be found in an in vivo reaction. Yet, the modified transposase described herein so increases the level of transposition activity that it is now possible to carry out this reaction in vitro where this has not previously been possible. The rates of reaction are even greater when the modified transposase is coupled with an optimized buffer and temperature conditions noted herein.

In another aspect, the present invention is a preparation of a modified Tn5 transposase enzyme that differs from wild type Tn5 transposase in that it (1) binds to the repeat sequences of the donor DNA with greater avidity than wild type Tn5 transposase and (2) is less likely than the wild type protein to assume an inactive multimeric form. An enzyme having these requirements can be obtained from a bacterial host cell containing an expressible gene for the modified enzyme that is under the control of a promoter active in the host cell. Genetic material that encodes the modified Tn5transposase can be introduced (e.g., by electroporation) into suitable bacterial host cells capable of supporting expression of the genetic material. Known methods for overproducing and preparing other Tn5 transposase mutants are suitably employed. For example, Weinreich, M. D., et al., supra, describes a suitable method for overproducing a Tn5 transposase. A second method for purifying Tn5 transposase was described in de la Cruz, N. B., et al., "Characterization of the Tn5 Transposase and Inhibitor Proteins: A Model for the Inhibition of Transposition," *J. Bact.* 175:6932–6938 (1993), also incorporated herein by reference. It is noted that induction can be carried out at temperatures below 37° C., which is the temperature used by de la Cruz, et al. Temperatures at least in the range of 33 to 37° C. are suitable. The inventors have determined that the method for preparing the modified transposase of the present invention is not critical to success of the method, as various preparation strategies have been used with equal success.

Alternatively, the protein can be chemically synthesized, in a manner known to the art, using the amino acid sequence attached hereto as SEQ ID NO:2 as a guide. It is also possible to prepare a genetic construct that encodes the modified protein (and associated transcription and translation signals) by using standard recombinant DNA methods familiar to molecular biologists. The genetic material useful for preparing such constructs can be obtained from existing Tn5 constructs, or can be prepared using known methods for introducing mutations into genetic material (e.g., random mutagenesis PCR or site-directed mutagenesis) or some combination of both methods. The genetic sequence that encodes the protein shown in SEQ ID NO:2 is set forth in SEQ ID NO:1.

The nucleic acid and amino acid sequence of wild type Tn5 transposase are known and published. N.C.B.I. Accession Number U00004 L19385, incorporated herein by reference.

In a preferred embodiment, the improved avidity of the modified transposase for the repeat sequences for OE termini (class (1) mutation) can be achieved by providing a lysine residue at amino acid 54, which is glutamic acid in wild type Tn5 transposase. The mutation strongly alters the preference of the transposase for OE termini, as opposed to inside end ("IE") termini. The higher binding of this mutation, known as EK54, to OE termini results in a transposition rate that is about 10-fold higher than is seen with wild type transposase. A similar change at position 54 to valine (mutant EV54) also results in somewhat increased binding/transposition for OE termini, as does a threonine-to-proline change at position 47 (mutant TP47; about 10-fold higher). It is believed that other, comparable transposase mutations (in one or more amino acids) that increase binding avidity for OE termini may also be obtained which would function as well or better in the in vitro assay described herein.

One of ordinary skill will also appreciate that changes to the nucleotide sequences of the short repeat sequences of the donor DNA may coordinate with other mutation(s) in or near the binding region of the transposase enzyme to achieve the same increased binding effect, and the resulting 5- to 50-fold increase in transposition rate. Thus, while the applicants have exemplified one case of a mutation that improves binding of the exemplified transposase, it will be understood that other mutations in the transposase, or in the short repeat sequences, or in both, will also yield transposases that fall within the scope and spirit of the present invention. A suitable method for determining the relative avidity for-Tn5 OE termini has been published by Jilk, R. A., et al., "The Organization of the Outside end of Transposon Tn5," *J. Bact.* 178:1671–79 (1996).

The transposase of the present invention is also less likely than the wild type protein to assume an inactive multimeric form. In the preferred embodiment, that class (2) mutation from wild type can be achieved by modifying amino acid 372 (leucine) of wild type Tn5 transposase to a proline (and, likewise by modifying the corresponding DNA to encode proline). This mutation, referred to as LP372, has previously been characterized as a mutation in the dimerization region of the transposase. Weinreich, et al., supra. It was noted by Weinreich et al. that this mutation at position 372 maps to a region shown previously to be critical for interaction with an inhibitor of Tn5 transposition. The inhibitor is a protein encoded by the same gene that encodes the transposase, but which is truncated at the N-terminal end of the protein, relative to the transposase. The approach of Weinreich et al. for determining the extent to which multimers are formed is suitable for determining whether a mutation falls within the scope of this element.

It is thought that when wild type Tn5 transposase multimerizes, its activity in trans is reduced. Presumably, a mutation in the dimerization region reduces or prevents multimerization, thereby reducing inhibitory activity and leading to levels of transposition 5- to 50-fold higher than are seen with the wild type transposase. The LP372 mutation achieves about 10-fold higher transposition levels than wild type. Likewise, other mutations (including mutations at a one or more amino acid) that reduce the ability of the transposase to multimerize would also function in the same manner as the single mutation at position 372, and would also be suitable in a transposase of the present invention. It may also be possible to reduce the ability of a Tn5 transposase to multimerize without altering the wild type sequence in the so-called dimerization region, for example by adding into the system another protein or non-protein agent that blocks the dimerization site. Alternatively, the dimerization region could be removed entirely from the transposase protein.

As was noted above, the inhibitor protein, encoded in partially overlapping sequence with the transposase, can interfere with transposase activity. As such, it is desired that the amount of inhibitor protein be reduced over the amount observed in wild type in vivo. For the present assay, the transposase is used in purified form, and it may be possible to separate the transposase from the inhibitor (for example, according to differences in size) before use. However, it is also possible to genetically eliminate the possibility of having any contaminating inhibitor protein present by removing its start codon from the gene that encodes the transposase.

An AUG in the wild type Tn5 transposase gene that encodes methionine at transposase amino acid 56 is the first codon of the inhibitor protein. However, it has already been shown that replacement of the methionine at position 56 has no apparent effect upon the transposase activity, but at the same time prevents translation of the inhibitor protein, thus resulting in a somewhat higher transposition rate. Weigand, T. W. and W. S. Reznikoff, "Characterization of Two Hypertransposing Tn5Mutants," *J. Bact.* 174:1229–1239 (1992), incorporated herein by reference. In particular, the present inventors have replaced the methionine with an alanine in the preferred embodiment (and have replaced the methionine-encoding AUG codon with an alanine-encoding GCC). A preferred transposase of the present invention therefore includes an amino acid other than methionine at amino acid position 56, although this change can be considered merely technically advantageous (since it ensures the absence of the inhibitor from the in vitro system) and not essential to the invention (since other means can be used to eliminate the inhibitor protein from the in vitro system).

The most preferred transposase amino acid sequence known to the inventors differs from the wild type at amino acid positions 54, 56, and 372. The mutations at positions 54 and 372 separately contribute approximately a 10-fold increase to the rate of transposition reaction in vivo. When the mutations are combined using standard recombinant techniques into a single molecule containing both classes of mutations, reaction rates of at least about 100-fold higher than can be achieved using wild type transposase are observed when the products of the in vitro system are tested in vivo. The mutation at position 56 does not directly affect the transposase activity.

Other mutants from wild type that are contemplated to be likely to contribute to high transposase activity in vitro include, but are not limited to glutaminic acid-to-lysine at position 110, and glutamic acid to lysine at position 345.

It is, of course, understood that other changes apart from these noted positions can be made to the modified transposase (or to a construct encoding the modified transposase) without adversely affecting the transposase activity. For example, it is well understood that a construct encoding such a transposase could include changes in the third position of codons such that the encoded amino acid does not differ from that described herein. In addition, certain codon changes have little or no functional effect upon the transposition activity of the encoded protein. Finally, other changes may be introduced which provide yet higher transposition activity in the encoded protein. It is also specifically envisioned that combinations of mutations can be combined to encode a modified transposase having even higher transposition activity than has been exemplified herein. All of these changes are within the scope of the present invention. It is noted, however, that a modified transposase containing the EK110 and EK345 mutations (both described by Weigand and Reznikoff, supra, had lower transposase activity than a transposase containing either mutation alone.

After the enzyme is prepared and purified, as described supra, it can be used in the in vitro transposition reaction described above to introduce any desired transposable element from a donor DNA into a target DNA. The donor DNA can be circular or can be linear. If the donor DNA is linear, it is preferred that the repeat sequences flanking the transposable element should not be at the termini of the linear fragment but should rather include some DNA upstream and downstream from the region flanked by the repeat sequences.

As was noted above, Tn5 transposition requires a pair of eighteen or nineteen base long termini. The wild type Tn5 outside end (OE) sequence (5'-CTGACTCTTATACACAAGT-3') (SEQ ID NO: 7) has been described. It has been discovered that a transposase-catalyzed in vitro transposition frequency at least as high as that of wild type OE is achieved if the termini in a construct include bases ATA at positions 10, 11, and 12, respectively, as well as the nucleotides in common between wild type OE and IE (e.g., at positions 1–3, 5–9, 13, 14, 16, and optionally 19). The nucleotides at positions 4, 15, 17, and 18 can correspond to the nucleotides found at those positions in either wild type OE or wild type IE. It is noted that the transposition frequency can be enhanced over that of wild type OE if the nucleotide at position 4 is a T. The importance of these particular bases to transposition frequency has not previously been identified.

It is noted that these changes are not intended to encompass every desirable modification to OE. As is described elsewhere herein, these attributes of acceptable termini modifications were identified by screening mutants having randomized differences between IE and OE termini. While the presence in the termini of certain nucleotides is shown herein to be advantageous, other desirable terminal sequences may yet be obtained by screening a larger array of degenerate mutants that include changes at positions other than those tested herein as well as mutants containing nucleotides not tested in the described screening. In addition, it is clear to one skilled in the art that if a different transposase is used, it may still be possible to select other variant termini, more compatible with that particular transposase.

Among the mutants shown to be desirable and within the scope of the invention are two hyperactive mutant OE sequences that were identified in vivo. Although presented here as single stranded sequences, in fact, the wild type and mutant OE sequences include complementary second strands. The first hyperactive mutant, 5'-CTGTCTCTTATACACATCT-3' (SEQ ID NO: 8), differs from the wild type OE sequence at positions 4, 17, and 18, counting from the 5' end, but retains ATA at positions 10–12. The second, 5'-CTGTCTCTTATACAGATCT-3' (SEQ ID NO: 9), differs from the wild type OE sequence at positions 4, 15, 17, and 18, but also retains ATA at positions 10–12. These two hyperactive mutant OE sequences differ from one another only at position 15, where either G or C is present. OE-like activity (or higher activity) is observed in a mutant sequence when it contains ATA at positions 10, 11 and 12. It may be possible to reduce the length of the OE sequence from 19 to 18 nucleotide pairs with little or no effect.

When one of the identified hyperactive mutant OE sequences flanks a substrate DNA, the in vivo transposition frequency of EK54/MA56 transposase is increased approximately 40–60 fold over the frequency that is observed when wild type OE termini flank the transposable DNA. The EK54/MA56 transposase is already known to have an in vivo transposition frequency approximately an 8–10 fold higher than wild type transposase, using wild type OE termini. Tn5 transposase having the EK54/MA56 mutation is known to bind with greater avidity to OE and with lesser avidity to the Tn5 inside ends (IE) than wild type transposase.

A suitable mutant terminus in a construct for use in the assays of the present invention is characterized biologically as yielding more papillae per colony in a comparable time, say 68 hours, than is observed in colonies harboring wild type OE in a comparable plasmid. Wild type OE can yield about 100 papillae per colony when measured 68 hours after plating in a papillation assay using EK54/MA56 transposase, as is described elsewhere herein. A preferred mutant would yield between about 200 and 3000 papillae per colony, and a more preferred mutant between about 1000 and 3000 papillae per colony, when measured in the same assay and time frame. A most preferred mutant would yield between about 2000 and 3000 papillae per colony when assayed under the same conditions. Papillation levels may be even greater than 3000 per colony, although it is difficult to quantitate at such levels.

Transposition frequency is also substantially enhanced in the in vitro transposition assay of the present invention when substrate DNA is flanked by a preferred mutant OE sequence and a most preferred mutant transposase (comprising EK54/MA56/LP372 mutations) is used. Under those conditions, essentially all of the substrate DNA is converted into transposition products.

The rate of in vitro transposition observed using the hyperactive termini is sufficiently high that, in the experience of the inventors, there is no need to select for transposition events. All colonies selected at random after transformation for further study have shown evidence of transposition events.

This advance can represent a significant savings in time and laboratory effort. For example, it is particularly advantageous to be able to improve in vitro transposition frequency by modifying DNA rather than by modifying the transposase because as transposase activity increases in host cells, there is an increased likelihood that cells containing the transposase are killed during growth as a result of aberrant DNA transpositions. In contrast, DNA of interest containing the modified OE termini can be grown in sources completely separate from the transposase, thus not putting the host cells at risk.

Without intending to limit the scope of this aspect of this invention, it is apparent that the tested hyperactive termini do not bind with greater avidity to the transposase than do wild type OE termini. Thus, the higher transposition frequency brought about by the hyperactive termini is not due to enhanced binding to transposase.

The transposable element between the termini can include any desired nucleotide sequence. The length of the transposable element between the termini should be at least about 50 base pairs, although smaller inserts may work. No upper limit to the insert size is known. However, it is known that a donor DNA portion of about 300 nucleotides in length can function well. By way of non-limiting examples, the transposable element can include a coding region that encodes a detectable or selectable protein, with or without associated regulatory elements such as promoter, terminator, or the like.

If the element includes such a detectable or selectable coding region without a promoter, it will be possible to identify and map promoters in the target DNA that are uncovered by transposition of the coding region into a position downstream thereof, followed by analysis of the nucleic acid sequences upstream from the transposition site.

Likewise, the element can include a primer binding site that can be transposed into the target DNA, to facilitate sequencing methods or other methods that rely upon the use of primers distributed throughout the target genetic material. Similarly, the method can be used to introduce a desired restriction enzyme site or polylinker, or a site suitable for another type of recombination, such as a cre-lox, into the target.

The invention can be better understood upon consideration of the following examples which are intended to be exemplary and not limiting on the invention.

EXAMPLES

To obtain the transposase modified at position 54, the first third of the coding region from an existing DNA clone that encodes the Tn5 transposase but not the inhibitor protein (MA56) was mutagenized according to known methods and DNA fragments containing the mutagenized portion were cloned to produce a library of plasmid clones containing a full length transposase gene. The clones making up the library were transformed into *E. coli* K-12 strain MDW320 bacteria which were plated and grown into colonies. Transposable elements provided in the bacteria on a separate plasmid contained a defective lacZ gene. The separate plasmid, pOXgen386, was described by Weinreich, M. et al., "A functional analysis of the Tn5 Transposase: Identification of Domains Required for DNA Binding and Dimerization," *J. Mol. Biol.* 241:166–177 (1993), incorporated herein by reference. Colonies having elevated transposase activity were selected by screening for blue (LacZ) spots in white colonies grown in the presence of X-gal. This papillation assay was described by Weinreich, et al. (1993), supra. The 5'-most third of Tn5 transposase genes from such colonies were sequenced to determine whether a mutation was responsible for the increase in transposase activity. It was determined that a mutation at position 54 to lysine (K) correlated well with the increase in transposase activity. Plasmid pRZ5412-EK54 contains lysine at position 54 as well as the described alanine at position 56.

The fragment containing the LP372 mutation was isolated from pRZ4870 (Weinreich et al (1994)) using restriction enzymes NheI and BglII, and were ligated into NheI-BglII cut pRZ5412-EK54 to form a recombinant gene having the mutations at positions 54, 56 and 372, as described herein and shown in SEQ ID NO:1. The gene was tested and shown to have at least about a one hundred fold increase in activity relative to wild type Tn5 transposase. Each of the mutants at positions 54 and 372 alone had about a 10-fold increase in transposase activity.

The modified transposase protein encoded by the triple-mutant recombinant gene was transferred into commercial T7 expression vector pET-21D (commercially available from Novagen, Madison, WI) by inserting a BspHI/SalI fragment into NhoI/XhoI fragment of the pET-21D vector. This cloning puts the modified transposase gene under the control of the T7 promoter, rather than the natural promoter of the transposase gene. The gene product was overproduced in BL21(DE3)pLysS bacterial host cells, which do not contain the binding site for the enzyme, by specific induction in a fermentation process after cell growth is complete. (See, Studier, F. W., et al., "Use of T7 RNA Polymerase to Direct Expression of Cloned Genes," *Methods Enzymol.* 185:60–89 (1990)). The transposase was partially purified using the method of de la Cruz, modified by inducing overproduction at 33 or 37° C. After purification, the enzyme preparation was stored at −70° C. in a storage buffer (10% glycerol, 0.7M NaCl, 20 mM Tris-HCl, pH 7.5, 0.1% Triton-X100 and 10 mM CHAPS) until use. This storage buffer is to be considered exemplary and not optimized.

A single plasmid (pRZTL1, FIG. 1) was constructed to serve as both donor and target DNA in this Example. The complete sequence of the pRZTL1 plasmid DNA is shown and described in SEQ ID NO:3. Plasmid pRZTL1 contains two Tn5 19 base pair OE termini in inverted orientation to each other. Immediately adjacent to one OE sequence is a gene that would encode tetracycline resistance, but for the lack of an upstream promoter. However, the gene is expressed if the tetracycline resistance gene is placed downstream of a transcribed region (e.g., under the control of the promoter that promotes transcription of the chloramphenicol resistance gene also present on pRZTL1). Thus, the test plasmid pRZTL1 can be assayed in vivo after the in vitro reaction to confirm that transposition has occurred. The plasmid pRZTL1 also includes an origin of replication in the transposable element, which ensures that all transposition products are plasmids that can replicate after introduction in host cells.

The following components were used in typical 20μl in vitro transposition reactions:

Modified transposase: 2_1(approximately 0.1_g enzyme/_1) in storage buffer (10% glycerol, 0.7M NaCl, 20 mM Tris-HCl, pH 7.5, 0.1% TRITON® X-100 (octylphenol ethylene oxide condensate) and 10 mM CHAPS.

Donor/Target DNA: 18 μl (approximately 1–2 μg) in reaction buffer (at final reation concentrations of 0.1 M potassium glutamate, 25 mM Tris acetate, pH 7.5, 10 mM $Mg^{2+}$-acetate, 50 μg/ml BSA, 0.5 mM β-mercatoethananol, 2 mM spermidine, 100 μg/ml tRNA).

At 20° C., the transposase was combined with pRZTL1 DNA for about 60 minutes. Then, the reaction volume was increased by adding two volumes of reaction buffer and the temperature was raised to 37° C. for 2–3 hours whereupon cleavage and strand transfer occurred.

Efficient in vitro transposition was shown to have occurred by in vivo and by in vitro methods. In vivo, many tetracycline-resistant colonies were observed after transferring the nucleic acid product of the reaction into DH5α bacterial cells. As noted, tetracycline resistance can only arise in this system if the transposable element is transposed downstream from an active promoter elsewhere on the plasmid. A typical transposition frequency was 0.1% of cells that received plasmid DNA, as determined by counting chloramphenicol resistant colonies. However, this number underestimates the total transposition event frequency because the detection system limits the target to 1/16 of the total.

Moreover, in vitro electrophoretic (1% agarose) and DNA sequencing analyses of DNA isolated from purified colonies revealed products of true transposition events, including both intramolecular and intermolecular events. Results of typical reactions using circular plasmid pRZTL1 substrates are shown in Lanes 4 & 5. Lane 6 of FIG. 2 shows the results obtained using linear plasmid pRZTL1 substrates.

The bands were revealed on 1% agarose gels by staining with a DNA-intercalating cyanine dye (SYBR® Green, FMC BioProducts) and were detected by using a quantitative gel and blot imaging device that excites fluorescently-labeled DNA with a scanning laser and records the fluorescent emissions in an image file for analysis (FluorImager® SI, Molecular Dynamics). In FIG. 2, lane 1 shows relaxed circle, linear, and closed circle versions of pRZTL1. Lanes 2 and 3 show intramolecular and intermolecular transposition products after in vitro transposition of pRZTL1, respectively. The products were purified from electroporated DH5α cells and were proven by size and sequence analysis to be genuine transposition products. Lanes 4 and 5 represent products of two independent in vitro reactions using a mixture of closed and relaxed circular test plasmid substrates. In lane 6, linear pRZTL1 (XhoI-cut) was the reaction substrate. Lane 7 includes a BstEII digest of lambda DNA as a molecular weight standard.

Figure 2:
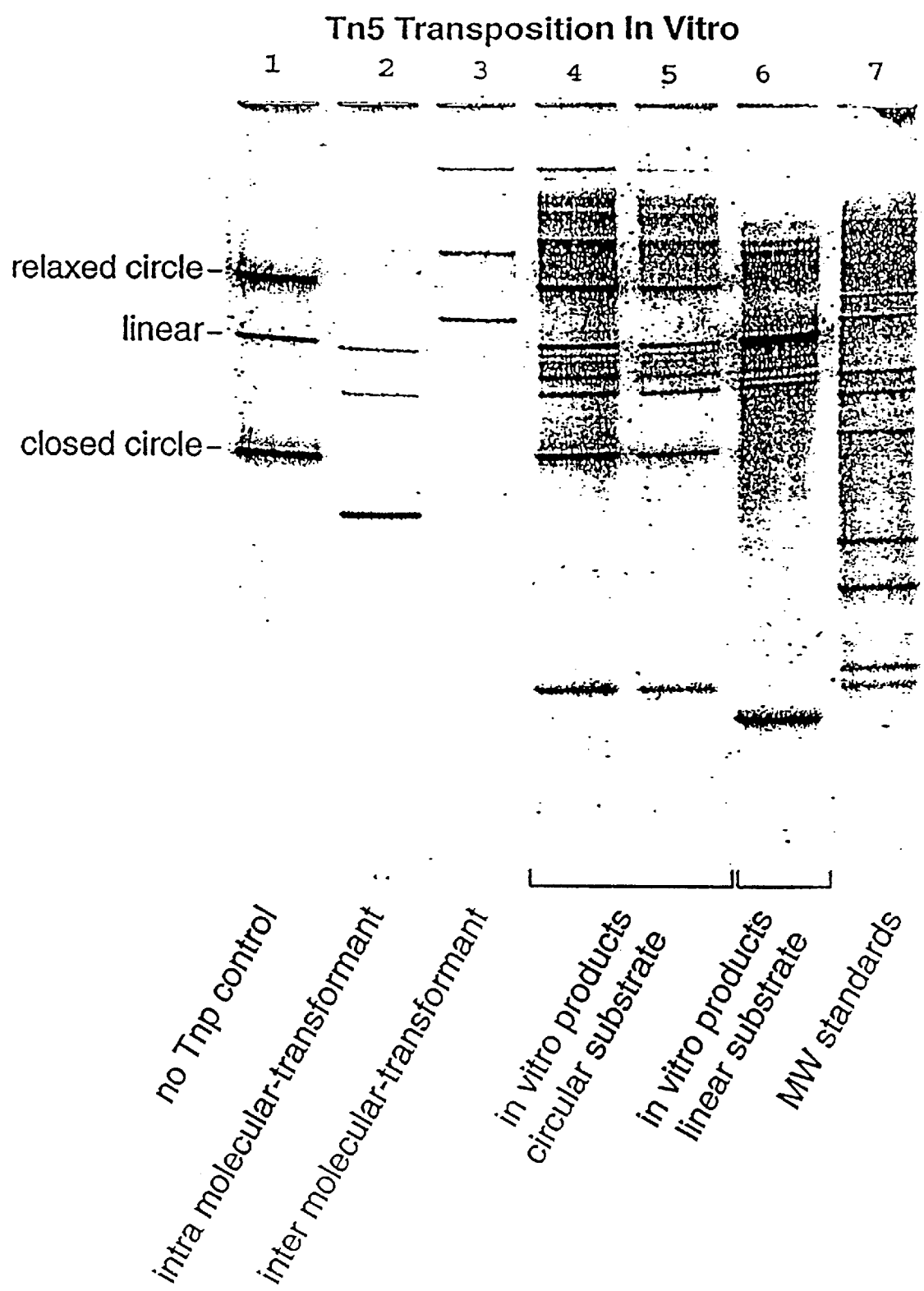
FIG. 2 depicts an electrophoretic analysis of plasmid pRZTL1 before and after in vitro transposition. Data obtained using both circular and linear plasmid substrates are shown.
Figure 3:
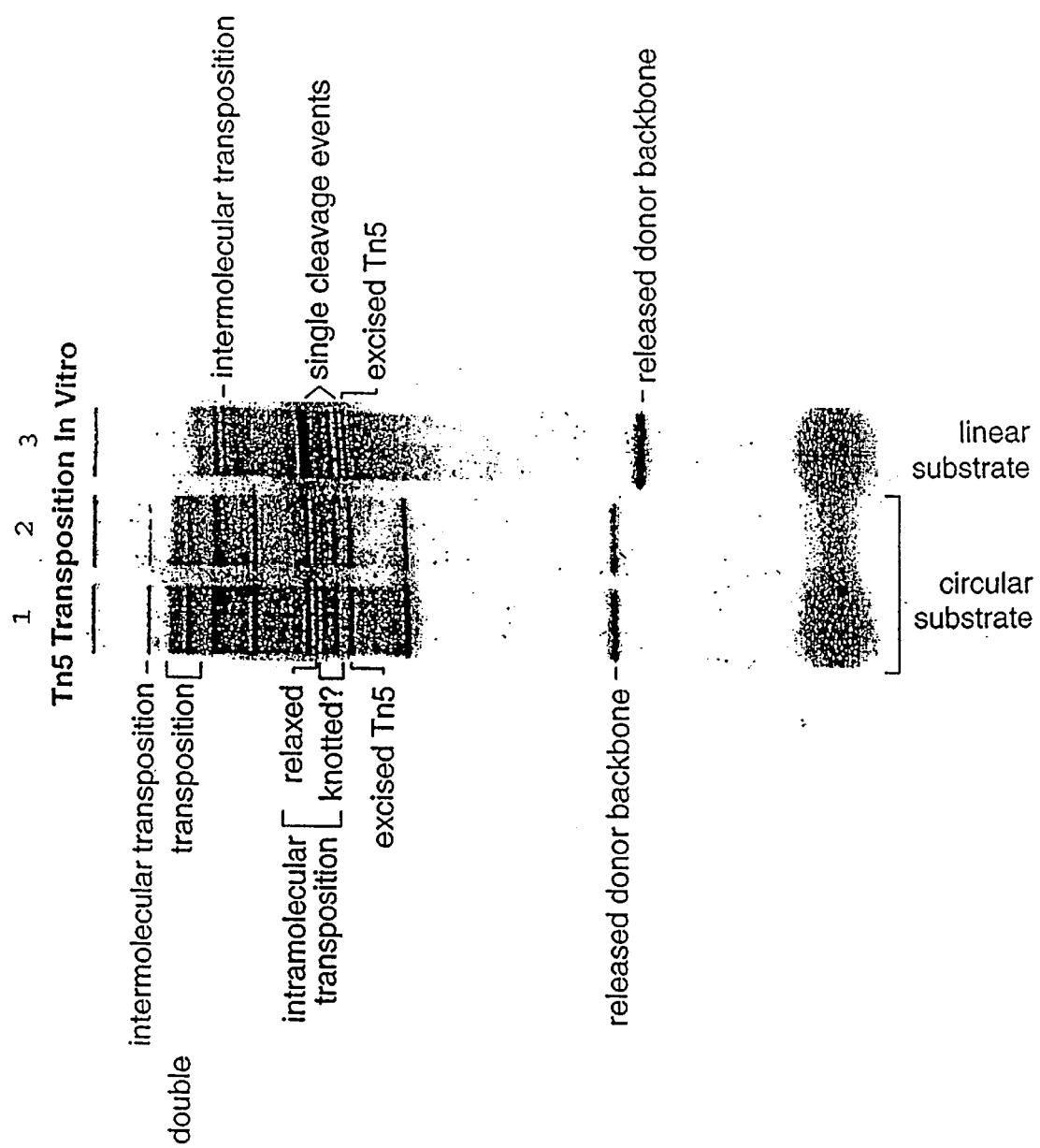
FIG. 3 is an electrophoretic analysis of plasmid pRZTL1 after in vitro transposition, including further analysis of the molecular species obtained using circular and linear plasmid substrates.

FIG. 3 reproduces lanes 4, 5, and 6 of FIG. 2 and shows an analysis of various products, based upon secondary restriction digest experiments and re-electroporation and DNA sequencing. The released donor DNA corresponds to the fragment of pRZTL1 that contains the kanamycin resistance gene between the two OE sequences, or, in the case of the linear substrate, the OE-XhoI fragment. Intermolecular transposition products can be seen only as relaxed DNA circles. Intramolecular transposition products are seen as a ladder, which results from conversion of the initial superhelicity of the substrate into DNA knots. The reaction is efficient enough to achieve double transposition events that are a combination of inter- and intramolecular events.

A preliminary investigation was made into the nature of the termini involved in a transposition reaction. Wild type Tn5 OE and IE sequences were compared and an effort was undertaken to randomize the nucleotides at each of the seven positions of difference. A population of oligonucleotides degenerate at each position of difference was created. Thus, individual oligonucleotides in the population randomly included either the nucleotide of the wild type OE or the wild type IE sequence. In this scheme, $2^7$ (128) distinct oligonucleotides were synthesized using conventional tools. These oligonucleotides having sequence characteristics of both OE and IE are referred to herein as OE/IE-like sequences. To avoid nomenclature issues that arise because the oligonucleotides are intermediate between OE and IE wild type sequences, the applicants herein note that selected oligonucleotide sequences are compared to the wild type OE rather than to wild type IE, unless specifically noted. It will be appreciated by one skilled in the art that if IE is selected as the reference point, the differences are identical but are identified differently.

The following depicts the positions (x) that were varied in this mutant production scheme. WT OE is shown also at SEQ ID NO: 7, WT IE at SEQ ID NO: 10.

5'-CTGACTCTTATACACAAGT-3' (WT OE)
    x xxx x xx (positions of difference)
5'-CTGTCTCTTGATCAGATCT-3' (WT IE)

In addition to the degenerate OE/IE-like sequences, the 37-base long synthetic oligonucleotides also included terminal SphI and KpnI restriction enzyme recognition and cleavage sites for convenient cloning of the degenerate oligonucleotides into plasmid vectors. Thus, a library of randomized termini was created from population of $2^7$ (128) types of degenerate oligonucleotides.

Figure 4:
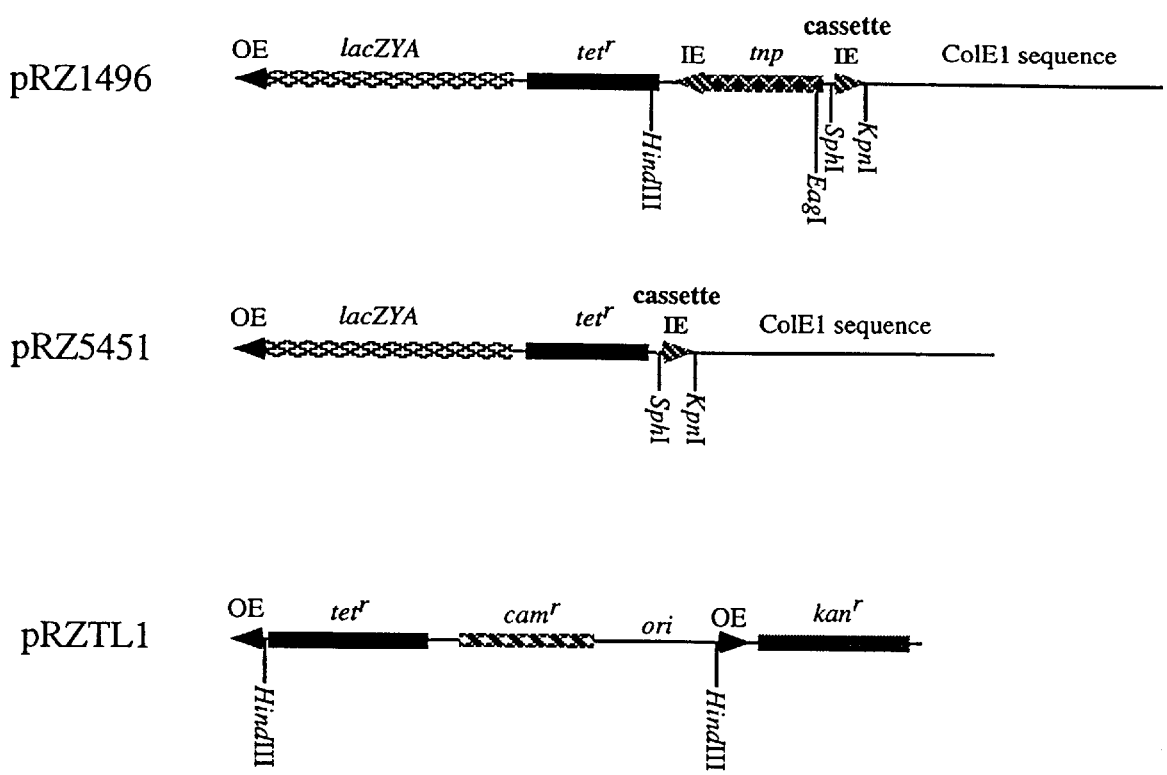
FIG. 4 shows plasmids pRZ1496, pRZ5451 and pRZTL1, which are detailed in the specification.

FIG. 4 shows pRZ1496, the complete sequence of which is presented as SEQ ID NO:11. The following features are noted in the sequence:

| Feature | Position |
|---|---|
| WT OE | 94–112 |
| LacZ coding | 135–3137 |
| LacY coding | 3199–4486 |
| LacA coding | 4553–6295 |
| tet$^r$ coding | 6669–9442 |
| transposase coding | 10683–12111 (Comp. Strand) |
| Cassette IE | 12184–12225 |
| colEl sequence | 127732–19182 |

The IE cassette shown in FIG. 4 was excised using SphI and KpnI and was replaced, using standard cleavage and ligation methods, by the synthetic termini cassettes comprising OE/IE-like portions. Between the fixed wild type OE sequence and the OE/IE-like cloned sequence, plasmid pRZ1496 comprises a gene whose activity can be detected, namely LacZYA, as well as a selectable marker gene, tet$^r$. The LacZ gene is defective in that it lacks suitable transcription and translation initiation signals. The LacZ gene is transcribed and translated only when it is transposed into a position downstream from such signals.

The resulting clones were transformed using electroporation into dam$^-$, LacZ$^-$ bacterial cells, in this case JCM101/pOXgen cells which were grown at 37° C. in LB medium under standard conditions. A dam$^-$ strain is preferred because dam methylation can inhibit IE utilization and wild type IE sequences include two dam methylation sites. A dam$^-$ strain eliminates dam methylation as a consideration in assessing transposition activity. The Tet$^r$ cells selected were LacZ$^-$; transposition-activated Lac expression was readily detectable against a negative background. pOXgen is a non-essential F factor derivative that need not be provided in the host cells.

In some experiments, the EK54/MA56 transposase was encoded directly by the transformed pRZ1496 plasmid. In other experiments, the pRZ1496 plasmid was modified by deleting a unique HindIII/EagI fragment (nucleotides 9112-12083) from the plasmid (see FIG. 4) to prevent transposase production. In the latter experiments, the host cells were co-transformed with the HindIII/EagI-deleted plasmid, termed pRZ5451 (FIG. 4), and with an EK54/MA56 transposase-encoding chloramphenicol-resistant plasmid. In some experiments, a comparable plasmid encoding a wild type Tn5 transposase was used for comparison.

Transposition frequency was assessed by a papillation assay that measured the number of blue spots (Lac producing cells or "papillae") in an otherwise white colony. Transformed cells were plated (approx. 50 colonies per plate) on Glucose minimal Miller medium (Miller, J., *Experiments in Molecular Genetics*, Cold Spring Harbor Laboratory, Cold Spring Harbor, N.Y. (1972)) containing 0.3% casamino acids, 5-bromo-4-chloro-3-indolyl-β-D-galactoside (40 μg/ml) and phenyl-β-D-galactoside (0.05%). The medium contained tetracycline (15 μg/ml) and, where needed, chloramphenicol (20 μg/ml). Colonies that survived the selection were evaluated for transposition frequency in vivo. Although colonies exhibiting superior papillation were readily apparent to the naked eye, the number of blue spots per colony were determined over a period of several days (approximately 90 hours post-plating).

To show that the high-papillation phenotype was conferred by the end mutations in the plasmids, colonies were re-streaked if they appeared to have papillation levels higher than was observed when wild type IE was included on the plasmid. Colonies picked from the streaked culture plates were themselves picked and cultured. DNA was obtained and purified from the cultured cells, using standard protocols, and was transformed again into "clean" JCM101/pOXgen cells. Papillation levels were again compared with wild type IE-containing plasmids in the above-noted assays, and consistent results were observed.

To obtain DNA for sequencing of the inserted oligonucleotide, cultures were grown from white portions of 117 hyperpapillating colonies, and DNA was prepared from each colony using standard DNA miniprep methods. The DNA sequence of the OE/IE-like portion of 117 clones was determined (42 from transformations using pRZ1496 as the cloning vehicle; 75 from transformations using pRZ5451 as the cloning vehicle). Only 29 unique mutants were observed. Many mutants were isolated multiple times. All mutants that showed the highest papillation frequencies contain OE-derived bases at positions 10, 11, and 12. When the OE-like bases at these positions were maintained, it was impossible to measure the effect on transposition of other changes, since the papillation level was already extremely high.

One thousand five hundred seventy five colonies were screened as described above. The likelihood that all 128 possible mutant sequences were screened was greater than 95%. Thus, it is unlikely that other termini that contribute to a greater transformation frequency will be obtained using the tested transposase.

TABLE I trans papillation level of hybrid end sequences with EK54 Tnp

| mutant | position | 1 | 2 | 3 | 4 | 5 | 6 | 7 | 8 | 9 | 10 | 11 | 12 | 13 | 14 | 15 | 16 | 17 | 18 | 19 | papillation level[a] | # of times isolated[b] |
|---|---|---|---|---|---|---|---|---|---|---|---|---|---|---|---|---|---|---|---|---|---|---|
| IE | | c | t | g | T | c | t | c | t | t | G | A | T | c | a | G | a | T | C | t | VL | 0 |
| OE | | | | | A | | | | | | A | T | A | | | C | | A | G | | M | 6 |
| 1 | | | | | | | | | | | A | T | A | | | | | | | | H | 2 |
| 2 | | | | | | | | | | | A | T | A | | | C | | | | | H | 3 |
| 3 | | | | | | | | | | | A | T | A | | | | | A | | | H | 5 |
| 4 | | | | | | | | | | | A | T | A | | | C | | A | | | H | 4 |
| 5 | | | | | | | | | | | A | T | A | | | C | | | G | | H | 6 |
| 6 | | | | | | | | | | | A | T | A | | | | | A | G | | H | 6 |
| 7 | | | | | | | | | | | A | T | A | | | C | | A | G | | H | 4 |
| 8 | | | | | | | | | | | A | T | A | | | | | | G | | M | 7 |

TABLE I-continued trans papillation level of hybrid end sequences with EK54 Tnp

| mutant position | 1 | 2 | 3 | 4 | 5 | 6 | 7 | 8 | 9 | 10 | 11 | 12 | 13 | 14 | 15 | 16 | 17 | 18 | 19 | papillation level[a] | # of times isolated[b] |
|---|---|---|---|---|---|---|---|---|---|---|---|---|---|---|---|---|---|---|---|---|---|
| 9  | | | | A | | | | | | A | T | A | | | |   | |   | | M | 3 |
| 10 | | | | A | | | | | | A | T | A | | | C | | |   | | M | 2 |
| 11 | | | | A | | | | | | A | T | A | | | |   | A |   | | M | 1 |
| 12 | | | | A | | | | | | A | T | A | | | |   |   | G | | | 0 |
| 13 | | | | A | | | | | | A | T | A | | | C |   | A |   | | | 0 |
| 14 | | | | A | | | | | | A | T | A | | | C |   |   | G | | M | 4 |
| 15 | | | | A | | | | | | A | T | A | | | |   | A | G | | M | 4 |
| 16 | | | |   | | | | | | A | T |   | | | C |   | A |   | | L | 2 |
| 17 | | | |   | | | | | | A | T |   | | | |   | A | G | | L | 1 |
| 18 | | | |   | | | | | | A | T |   | | | C |   | A | G | | L | 2 |
| 19 | | | |   | | | | | | A |   |   | | | C |   | A | G | | L | 1 |
| 20 | | | |   | | | | | |   | T |   | | | C |   | A | G | | L | 1 |
| 21 | | | |   | | | | | |   |   |   | | | C |   | A | G | | L | 1 |

All hybrid end sequences isolated on pRZ5451 that papillate more frequently than wt IE, when the EK54 Tnp is expressed from pFMA187, are listed.
[a]trans papillation levels of wt IE, wt OE and hybrid end sequences are classified as follows: VL-very low, L-low, M-medium, and H-high.
[b]Although mutants 12 and 13 were not found in this experiment, they were found in cis papillation screening (Table II).

TABLE II cis papillation level of hybrid end sequences with EK54 Tnp

| mutant position | 1 | 2 | 3 | 4 | 5 | 6 | 7 | 8 | 9 | 10 | 11 | 12 | 13 | 14 | 15 | 16 | 17 | 18 | 19 | papillation level[a] | # of times isolated[b] |
|---|---|---|---|---|---|---|---|---|---|---|---|---|---|---|---|---|---|---|---|---|---|
| IE | c | t | g | T | c | t | c | t | t | G | A | T | c | a | G | a | T | C | t | L | 0 |
| OE | | | | A | | | | | | A | T | A | | | C |   | A | G | | H | 2 |
| 1  | | | |   | | | | | | A | T | A | | | |   |   |   | | H | 2 |
| 2  | | | |   | | | | | | A | T | A | | | C |   |   |   | | | 0 |
| 3  | | | |   | | | | | | A | T | A | | | |   | A |   | | H | 1 |
| 4  | | | |   | | | | | | A | T | A | | | C |   | A |   | | H | 1 |
| 5  | | | |   | | | | | | A | T | A | | | C |   |   | G | | H | 1 |
| 6  | | | |   | | | | | | A | T | A | | | |   | A | G | | H | 2 |
| 7  | | | |   | | | | | | A | T | A | | | C |   | A | G | | H | 3 |
| 8  | | | |   | | | | | | A | T | A | | | |   |   | G | | H | 1 |
| 9  | | | | A | | | | | | A | T | A | | | |   |   |   | | H | 1 |
| 10 | | | | A | | | | | | A | T | A | | | C |   |   |   | | | 0 |
| 11 | | | | A | | | | | | A | T | A | | | |   | A |   | | H | 2 |
| 12 | | | | A | | | | | | A | T | A | | | |   |   | G | | MH | 3 |
| 13 | | | | A | | | | | | A | T | A | | | C |   | A |   | | MH | 1 |
| 14 | | | | A | | | | | | A | T | A | | | C |   |   | G | | | 0 |
| 15 | | | | A | | | | | | A | T | A | | | |   | A | G | | H | 2 |
| 16 | | | |   | | | | | | A | T |   | | | C |   |   |   | | M | 1 |
| 17 | | | |   | | | | | | A | T |   | | | |   | A | G | | M | 1 |
| 18 | | | | A | | | | | | A | T |   | | | C |   |   |   | | M | 2 |
| 19 | | | | A | | | | | | A | T |   | | | C |   | A |   | | M | 2 |
| 20 | | | | A | | | | | | A | T |   | | | C |   | A | G | | M | 1 |
| 21 | | | |   | | | | | | A |   | A | | | |   | A |   | | M | 4 |
| 22 | | | |   | | | | | | A |   | A | | | |   |   | G | | M | 1 |
| 23 | | | |   | | | | | | A |   | A | | | C |   | A | G | | M | 1 |
| 24 | | | |   | | | | | | A |   |   | | | C |   | A |   | | M | 1 |
| 25 | | | |   | | | | | | A |   |   | | | C |   | A | G | | M | 1 |
| 26 | | | |   | | | | | |   | T |   | | | C |   | A | G | | M | 1 |
| 27 | | | |   | | | | | |   |   |   | | | C |   | A | G | | M | 2 |

All hybrid end sequences isolated on pRZ1496 that papillate more frequently than wt IE, when the EK54 Tnp is expressed from the same plasmid, are listed.
[a] cis papillation levels of wt IE, wt OE and hybrid end sequences are classified as follows: L-low, M-medium, MH-medium high, and H-high.
[b]Although mutants 2, 10 and 14 were not found in this experiment, they were found in trans papillation screening (Table I).

Tables I and II report the qualitative papillation level of mutant constructs carrying the indicated hybrid end sequences or the wild type OE or IE end sequences. In the tables, the sequence at each position of the terminus corresponds to wild type IE unless otherwise noted. The applicants intend that, while the sequences are presented in shorthand notation, one of ordinary skill can readily determine the complete 19 base pair sequence of every presented mutant, and this specification is to be read to include all such complete sequences. Table I includes data from trials where the EK54 transposase was provided in trans; Table II, from those trials where the EK54 transposase was provided in cis.

Although a transposase provided in cis is more active in absolute terms than a transposase provided in trans, the cis or trans source of the transposase does not alter the relative in vivo transposition frequencies of the tested termini.

Tables I and II show that every mutant that retains ATA at positions 10, 11, and 12, respectively, had an activity comparable to, or higher than, wild type OE, regardless of whether the wild type OE activity was medium (Table I, trans) or high (Table II, cis). Moreover, whenever that three-base sequence in a mutant was not ATA, the mutant exhibited lower papillation activity than wild type OE. It was also noted that papillation is at least comparable to, and tends to be significantly higher than, wild type OE when position 4 is a T.

Quantitative analysis of papillation levels was difficult, beyond the comparative levels shown (very low, low, medium, medium high, and high). However, one skilled in the art can readily note the papillation level of OE and can recognize those colonies having comparable or higher levels. It is helpful to observe the papillae with magnification.

Figure 5:
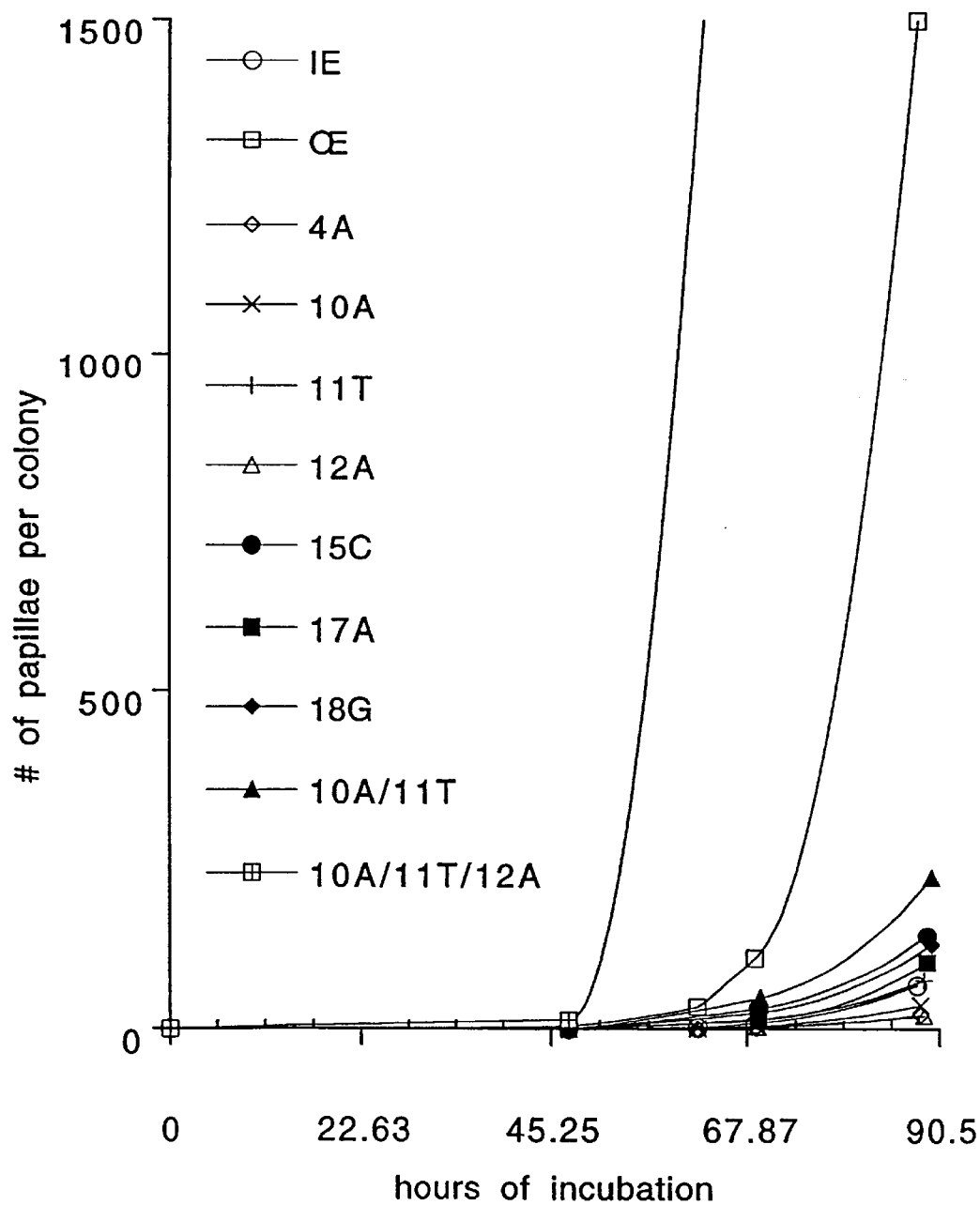
FIG. 5 shows a plot of papillae per colony over time for various mutant OE sequences tested in vivo against EK54/MA56 transposase.
Figure 6:
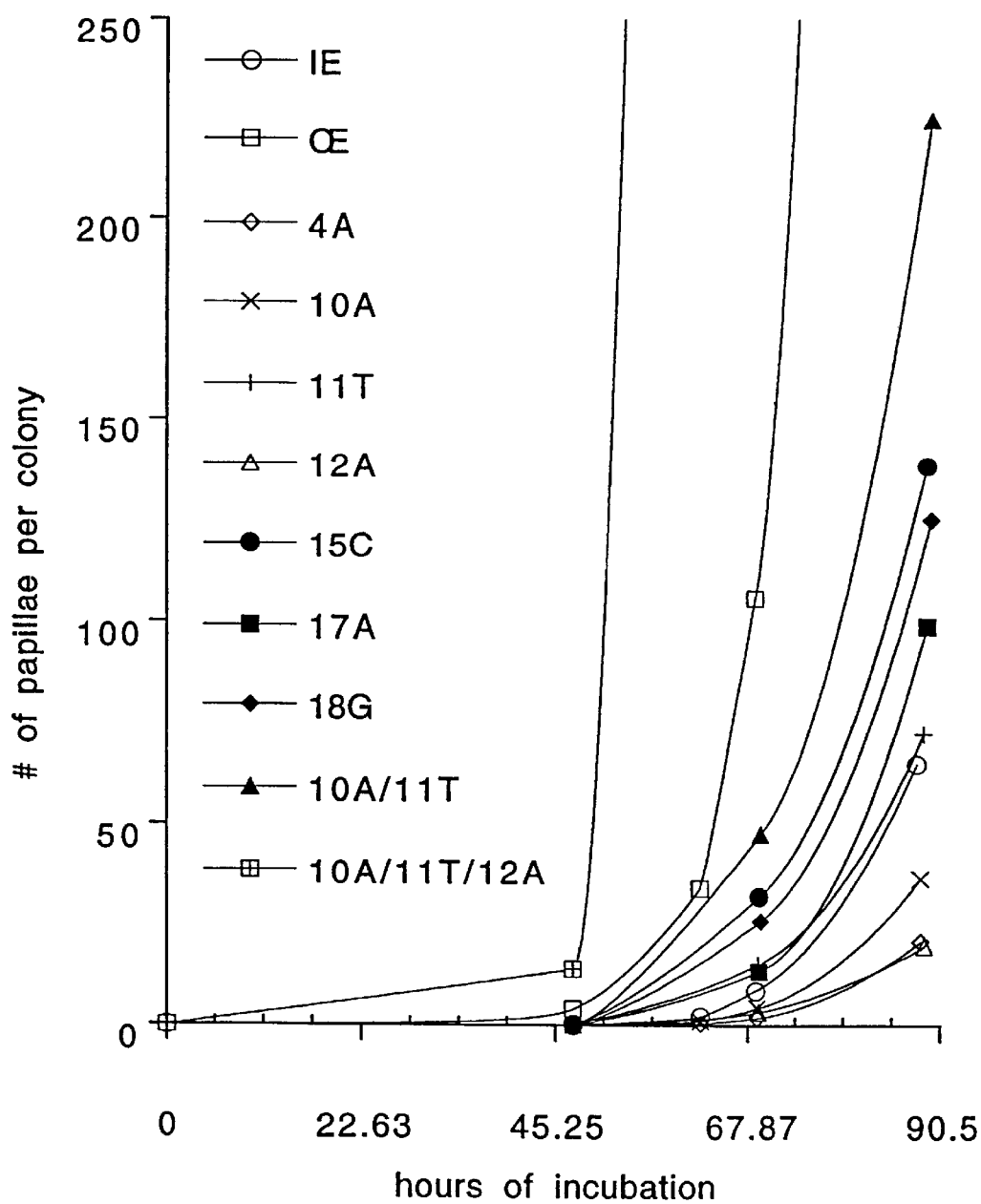
FIG. 6 shows a plot of papillae per colony over time for various mutant OE sequences with a smaller Y-axis than is shown in FIG. 5 tested against EK54/MA56 transposase.
Figure 7:
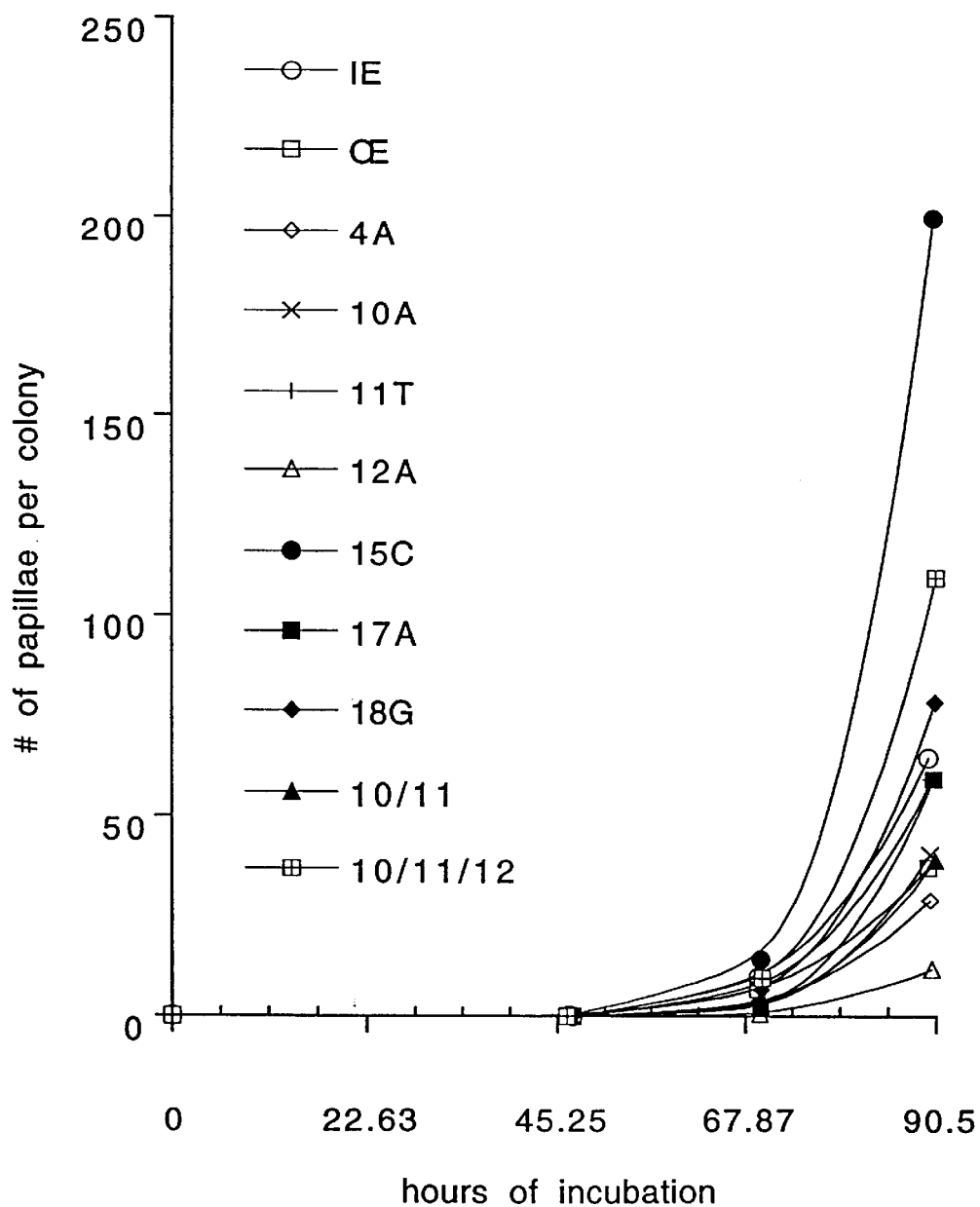
FIG. 7 shows a plot of papillae per colony over time for various mutant OE sequences tested against MA56 Tn5 transposase.

The number of observed papillae increased over time, as is shown in FIGS. 5–7 which roughly quantitate the papillation observed in cells transformed separately with 9 clones containing either distinct synthetic termini cassettes or wild type OE or IE termini. In these 3 figures, each mutant is identified by its differences from the wild type IE sequence. Note that, among the tested mutants, only mutant 10A/11T/12A had a higher transposition papillation level than wild type OE. That mutant, which would be called mutant 4/15/17/18 when OE is the reference sequence) was the only mutant of those shown in FIGS. 5–7 that retained the nucleotides ATA at positions 10, 11, and 12. FIG. 5 (y-axis: 0–1500 papillae) and 6 (y-axis: 0–250 papillae) show papillation using various mutants plus IE and OE controls and the EK54/MA56 enzyme. FIG. 7 (y-axis: 0–250 papillae), shows papillation when the same mutant sequences were tested against the wild type (more properly, MA56) transposase. The 10A/11T/12A mutant (SEQ ID NO: 9) yielded significantly more papillae (approximately 3000) in a shorter time (68 hours) with ED54/MA56 transposase than was observed even after 90 hours with the WT OE (approximately 1500). A single OE-like nucleotide at position 15 on an IE-like background also increased papillation frequency.

In vivo transposition frequency was also quantitated in a tetracycline-resistance assay using two sequences having high levels of hyperpapillation. These sequences were 5'-CTGTCTCTTATACACATCT-3' (SEQ ID NO: 8), which differs from the wild type OE sequence at positions 4, 17, and 18, counting from the 5' end, and 5'-CTGTCTCTTATACAGATCT-3' (SEQ ID NO: 9), which differs from the wild type OE at positions 4, 15, 17, and 18. These sequences are considered the preferred mutant termini in an assay using a transposase that contains EK54/MA56 or a transposase that contains MA56. Each sequence was separately engineered into pRZTL1 in place of the plasmid's two wild type OE sequences. A PCR-amplified fragment containing the desired ends flanking the kanamycin resistance gene was readily cloned into the large HindIII fragment of pRZTL1. The resulting plasmids are identical to pRZTL1 except at the indicated termini. For comparison, pRZTL1 and a derivative of pRZTL1 containing two wild type IE sequences were also tested. In the assay, JCM101/pOXgen cells were co-transformed with a test plasmid (pRZTL1 or derivative) and a high copy number amp$^r$ plasmid that encoded either the EK54/MA56 transposase or wild type (MA56) transposase. The host cells become tetracycline resistant only when a transposition event brings the Tet$^r$ gene into downstream proximity with a suitable transcriptional promoter elsewhere on a plasmid or on the chromosome. The total number of cells that received the test plasmids was determined by counting chloramphenicol resistant, ampicillin resistant colonies. Transposition frequency was calculated by taking the ratio of tet$^r$/cam$^r$amp$^r$ colonies. Approximately 40 to 60 fold increase over wild type OE in in vivo transposition was observed when using either of the mutant termini and EK54/MA56 transposase. Of the two preferred mutant termini, the one containing mutations at three positions relative to the wild type OE sequence yielded a higher increase.

Figure 8:
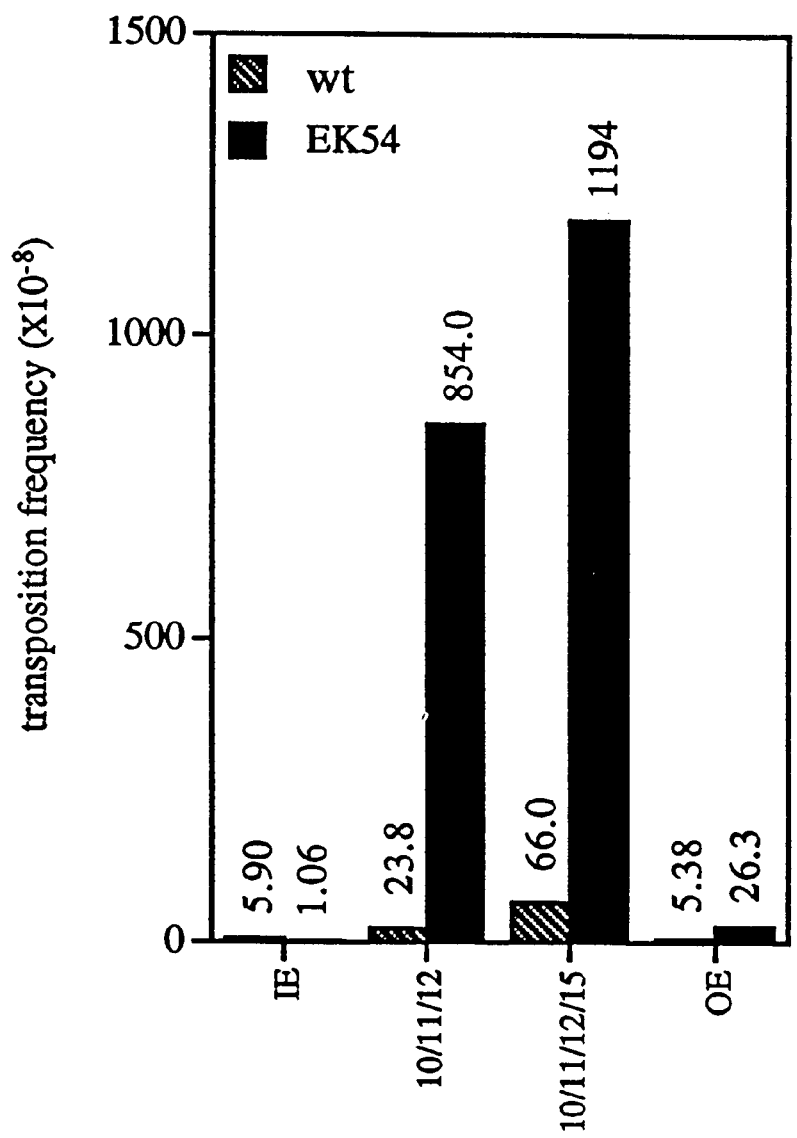
FIG. 8 shows in vivo transposition using two preferred mutants, tested against MA56 and EK54/MA56 transposase.

As is shown in FIG. 8, which plots the tested plasmid against the transposition frequency ($\times 10^{-8}$), little transposition was seen when the test plasmid included two IE termini. Somewhat higher transposition was observed when the test plasmid included two OE termini, particularly when the EK54/MA56 transposase was employed. In striking contrast, the combination of the EK54/MA56 transposase with either of the preferred selected ends (containing OE-like bases only at positions 10, 11, and 12, or positions 10, 11, 12, and 15) yielded a great increase in in vivo transposition over wild type OE termini.

The preferred hyperactive mutant terminus having the most preferred synthetic terminus sequence 5'-CTGTCTCTTATACACATCT-3' (SEQ ID NO: 8) was provided in place of both WT OE termini in pRZTL1 (FIG. 4) and was tested in the in vitro transposition assay of the present invention using the triple mutant transposase described herein. This mutant terminus was chosen for further in vitro analysis because its transposition frequency was higher than for the second preferred synthetic terminus and because it has no dam methylation sites, so dam methylation no longer affects transposition frequency. In contrast the 4/15/17/18 mutant does have a dam methylation site.

In a preliminary experiment, CHAPS was eliminated from the reaction, but the pre-incubation step was used. The reaction was pre-incubated for 1 hour at 20° C., then diluted two times, and then incubated for 3 hours at 37° C. About 0.5 µg of DNA and 0.4 µg of transposase was used. The transposition products were observed on a gel. With the mutant termini, very little of the initial DNA was observed. Numerous bands representing primary and secondary transposition reaction products were observed. The reaction mixtures were transformed into DH5α cells and were plated on chloramphenicol-, tetracycline-, or kanamycin-containing plates.

Six hundred forty chloramphenicol-resistant colonies were observed. Although these could represent unreacted plasmid, all such colonies tested (n=12) were sensitive to kanamycin, which indicates a loss of donor backbone DNA. All twelve colonies also included plasmids of varied size; 9 of the 12 were characterized as deletion-inversions, the remaining 3 were simple deletions. Seventy nine tetracycline-resistant colonies were observed, which indicated an activation of the tet$^r$ gene by transposition.

Eleven kanamycin resistant colonies were observed. This indicated a low percentage of remaining plasmids carrying the donor backbone DNA.

In a second, similar test, about 1 µg of plasmid DNA and 0.2 µg transposase were used. In this test, the reaction was incubated without CHAPS at 37° C. for 3 hours without pre-incubation or dilution. Some initial DNA was observed in the gel after the 3 hour reaction. After overnight incubation, only transposition products were observed.

The 3 hour reaction products were transformed into DH5α cells and plated as described. About 50% of the chloramphenicol resistant colonies were sensitive to kanamycin and were presumably transposition products.

The invention is not intended to be limited to the foregoing examples, but to encompass all such modifications and variations as come within the scope of the appended claims.

It is envisioned that, in addition to the uses specifically noted herein, other applications will be apparent to the skilled molecular biologist. In particular, methods for introducing desired mutations into prokaryotic or eukaryotic DNA are very desirable. For example, at present it is difficult to knock out a functional eukaryotic gene by homologous recombination with an inactive version of the gene that resides on a plasmid. The difficulty arises from the need to flank the gene on the plasmid with extensive upstream and downstream sequences. Using this system, however, an inactivating transposable element containing a selectable marker gene (e.g., neo) can be introduced in vitro into a plasmid that contains the gene that one desires to inactivate. After transposition, the products can be introduced into suitable host cells. Using standard selection means, one can recover only cell colonies that contain a plasmid having the transposable element. Such plasmids can be screened, for example by restriction analysis, to recover those that contain a disrupted gene. Such clones can then be introduced directly into eukaryotic cells for homologous recombination and selection using the same marker gene.

Also, one can use the system to readily insert a PCR-amplified DNA fragment into a vector, thus avoiding traditional cloning steps entirely. This can be accomplished by (1) providing suitable a pair of PCR primers containing OE termini adjacent to the sequence-specific parts of the primers, (2) performing standard PCR amplification of a desired nucleic acid fragment, (3) performing the in vitro transposition reaction of the present invention using the double-stranded products of PCR amplification as the donor DNA.

We claim:

1. A genetic construct comprising:
   a transposable DNA sequence flanked at its 5' and 3' end by an 18 or 19 base pair flanking DNA sequence comprising nucleotide A at position 10, nucleotide T at position 11, and nucleotide A at position 12, wherein the flanking DNA sequence differs from wild-type Tn5 outside end sequence (SEQ ID NO: 7) in at least one base pair selected from the group consisting of bases pairs 4, 15, 17 and 18.

2. The construct of claim 1 further comprising, at position 4 of the flanking sequence, a nucleotide selected from the group consisting of T and A.

3. The construct of claim 1 further comprising, at position 15 of the flanking sequence, a nucleotide selected from the group consisting of G and C.

4. The construct of claim 1 further comprising, at position 17 of the flanking sequence, a nucleotide selected from the group consisting of T and A.

5. The construct of claim 1 further comprising, at position 18 of the flanking sequence, a nucleotide selected from the group consisting of G and C.

6. The construct as claimed in claim 1 wherein the flanking sequence has the sequence 5'-CTGTCTCTTATACACATCT-3' (SEQ ID NO: 8).

7. The construct as claimed in claim 1 wherein the flanking sequence has the sequence 5'-CTGTCTCTTATACAGATCT-3' (SEQ ID NO: 9).

* * * * *